(12) United States Patent
Hoffmann et al.

(10) Patent No.: US 11,944,409 B2
(45) Date of Patent: Apr. 2, 2024

(54) WEARABLE DEVICE FOR THREAT EVALUATION AND DATA COLLECTION

(71) Applicant: HDWB, LLC, El Paso, TX (US)

(72) Inventors: Eric William Hoffmann, Saint Francis, WI (US); John Myrl Warren, El Paso, TX (US); Nicholas M Hall, El Paso, TX (US)

(73) Assignee: HDWB, LLC, El Paso, TX (US)

( * ) Notice: Subject to any disclaimer, the term of this patent is extended or adjusted under 35 U.S.C. 154(b) by 0 days.

(21) Appl. No.: 17/368,547

(22) Filed: Jul. 6, 2021

(65) Prior Publication Data

US 2021/0330194 A1 Oct. 28, 2021

Related U.S. Application Data

(63) Continuation-in-part of application No. 16/513,738, filed on Jul. 17, 2019, now Pat. No. 11,057,688.

(60) Provisional application No. 62/700,532, filed on Jul. 19, 2018.

(51) Int. Cl.
*A61B 5/0205* (2006.01)
*A61B 5/00* (2006.01)

(52) U.S. Cl.
CPC .......... *A61B 5/0205* (2013.01); *A61B 5/0022* (2013.01); *A61B 5/0024* (2013.01); *A61B 5/6802* (2013.01); *A61B 5/7246* (2013.01); *A61B 2560/0242* (2013.01)

(58) Field of Classification Search
CPC ... A61B 5/0205; A61B 5/0022; A61B 5/0024; A61B 5/6802; A61B 5/7246; A61B 2560/0242; H04Q 2209/10; H04Q 2209/40; H04Q 2209/50; H04Q 2209/823; H04Q 9/00
See application file for complete search history.

(56) References Cited

U.S. PATENT DOCUMENTS

| | | | | |
|---|---|---|---|---|
| 10,096,234 | B1* | 10/2018 | Chun | G08B 21/0283 |
| 2008/0001735 | A1* | 1/2008 | Tran | A61B 5/6806 340/539.22 |
| 2013/0194066 | A1* | 8/2013 | Rahman | G05B 1/01 340/5.51 |
| 2014/0285113 | A1* | 9/2014 | Huang | H05B 47/19 315/297 |
| 2015/0189403 | A1* | 7/2015 | Magi | A44C 5/0015 340/870.07 |
| 2017/0119318 | A1* | 5/2017 | Shay | A61B 5/05 |

(Continued)

*Primary Examiner* — Amine Benlagsir
(74) *Attorney, Agent, or Firm* — Georgiy L. Khayet

(57) ABSTRACT

Systems and methods for threat evaluation and data collection are described herein. An example method may commence with collecting, by a wearable device, sensor data from one or more sensors installed on the wearable device. The wearable device may be worn by a user and be communicatively coupled to a central data portal and one or more external sources. The method may include receiving external sensor data from the one or more external sources. The method may continue with processing the sensor data and the external sensor data to evaluate a user state. The user state may be indicative of at least one physical threat to the user or at least one medical condition of the user. The method may further include transmitting the user state to the central data portal. The central data portal may be configured to process the user state for storage and visualization.

18 Claims, 18 Drawing Sheets

(56) References Cited

U.S. PATENT DOCUMENTS

2018/0190017 A1\* 7/2018 Mendez .................. G06T 17/00
2018/0283825 A1\* 10/2018 Daly ......................... F41G 3/26

\* cited by examiner

WEARABLE DEVICE FOR THREAT EVALUATION AND DATA COLLECTION

CROSS-REFERENCE TO RELATED APPLICATIONS

This application is a Continuation-in-Part of U.S. application Ser. No. 16/513,738 filed on Jul. 17, 2019 entitled "Methods and systems for evaluating and transmitting combined external data from one or more sources to a central data portal for processing, storage, and visualization," which claims benefit of priority of U.S. Provisional Patent Application No. 62/700,532 filed on Jul. 19, 2018 entitled "Methods and system for the evaluation and transmission of combined external data from one or more sources to a central data portal for processing, storage, and visualization." The subject matter of the aforementioned applications is incorporated herein by reference in its entirety.

TECHNICAL FIELD

The present disclosure relates generally to data processing and, more specifically, to wearable devices for threat evaluation and data collection.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

Existing systems for the transmission of external data are employed independently of each other and, therefore, are limited in their ability to collect or combine information from different and multiple data sources for transmission and evaluation using a single data transmission source.

Existing systems operating in the telemetry space are also constrained by limited modes or limited combinations of modes for data transmission. These limitations can prevent combining data from different multiple sources at a single data portal for the processing, storage, and visualization of the data. Thus, data related to persons, vehicles, machineries, assets, buildings, or external environments are treated as separate entities during processing, storing, and visualization while aggregated at a centralized data portal.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are computer-implemented systems and methods for threat evaluation and data collection. According to one example embodiment, a wearable device for threat evaluation and data collection is provided. The wearable device may be configured to be worn by a user. The wearable device may include a processor, a sensor unit configured to receive sensor data from one or more sensors installed on the wearable device, and a communication unit communicatively coupled to a central data portal and one or more external sources. The wearable device may further include a housing to hold the processor, the sensor unit, and the communication unit. The housing may be carried out in one of the following shapes: glasses, a watch, a ring, a necklace, and so forth.

The processor may be configured to receive the sensor data from the sensor unit and receive external sensor data from the one or more external sources via the communication unit. The one or more sensors may be configured to measure at least one physiological parameter of the user. The processor may be further configured to process the sensor data and the external sensor data to evaluate a user state. The evaluation of the user state may include detecting a sudden change in the at least one physiological parameter. The at least one physiological parameter includes one of the following: a heart rate, a blood pressure, an electrocardiogram, a blood oxygen saturation level, and so forth.

The user state may be indicative of at least one physical threat to the user or at least one medical condition of the user. In an example embodiment, the one or more sensors may be configured to measure one or more of the following: a position and a motion of the user. In this embodiment, the evaluation of the user state may include detecting a sudden change of the position or the motion of the user. The processor may be further configured to transmit the user state to the central data portal. The central data portal may be configured to process the user state for storage and visualization.

In an example embodiment, the communication unit may be communicatively connected to a stationary hospital device. The processor may be configured to collect, via the communication unit, data from the stationary hospital device and transmit the data from the stationary hospital device to the central data portal.

In an example embodiment, the processor may be configured to determine or actuate statuses of the one or more external sources. The one or more external sources may include one of the following: a building, a room, an outdoor location, a car, and a personal computing device of the user. The processor may be configured to determine the user state based on a correlation between the statuses of the one or more external sources. The statuses may include one of the following: a humidity level at the outdoor location outside of a pre-determined humidity range, an air temperature at the outdoor location outside of a pre-determined temperature range, an air quality level at the outdoor location outside of a pre-determined air quality range, a gunshot detected at the outdoor location, a smoke detector alarm at the outdoor location, a gas detector alarm at the outdoor location, an unlocked room, a locked room, an open window, a closed window, a temperature of the room higher than a pre-determined temperature threshold, a smoke detector alarm, a gas detector alarm in the building, a fire detector alarm in the building, a humidity level in the room outside a pre-determined humidity range, an air quality level in the room outside a pre-determined air quality range, a gunshot in the building or the room detected, a window glass broken, a door impacted, a wall impacted, and so forth.

According to another example embodiment, a method for threat evaluation and data collection is provided. The method may commence with collecting, by a wearable device, sensor data from one or more sensors installed on the wearable device. The wearable device may be worn by a user and may include a processor, a sensor unit, and a communication unit communicatively coupled to a central data portal and one or more external sources. The method may include receiving, by the wearable device, external sensor data from the one or more external sources. The method may continue with processing, by the wearable device, the sensor data and the external sensor data to evaluate a user state. The user state may be indicative of at least one physical threat to the user or at least one medical condition of the user. The method may further include transmitting, by the wearable device, the user state to the central data portal. The central data portal may be configured to process the user state for storage and visualization.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

DETAILED DESCRIPTION

Figure 1:
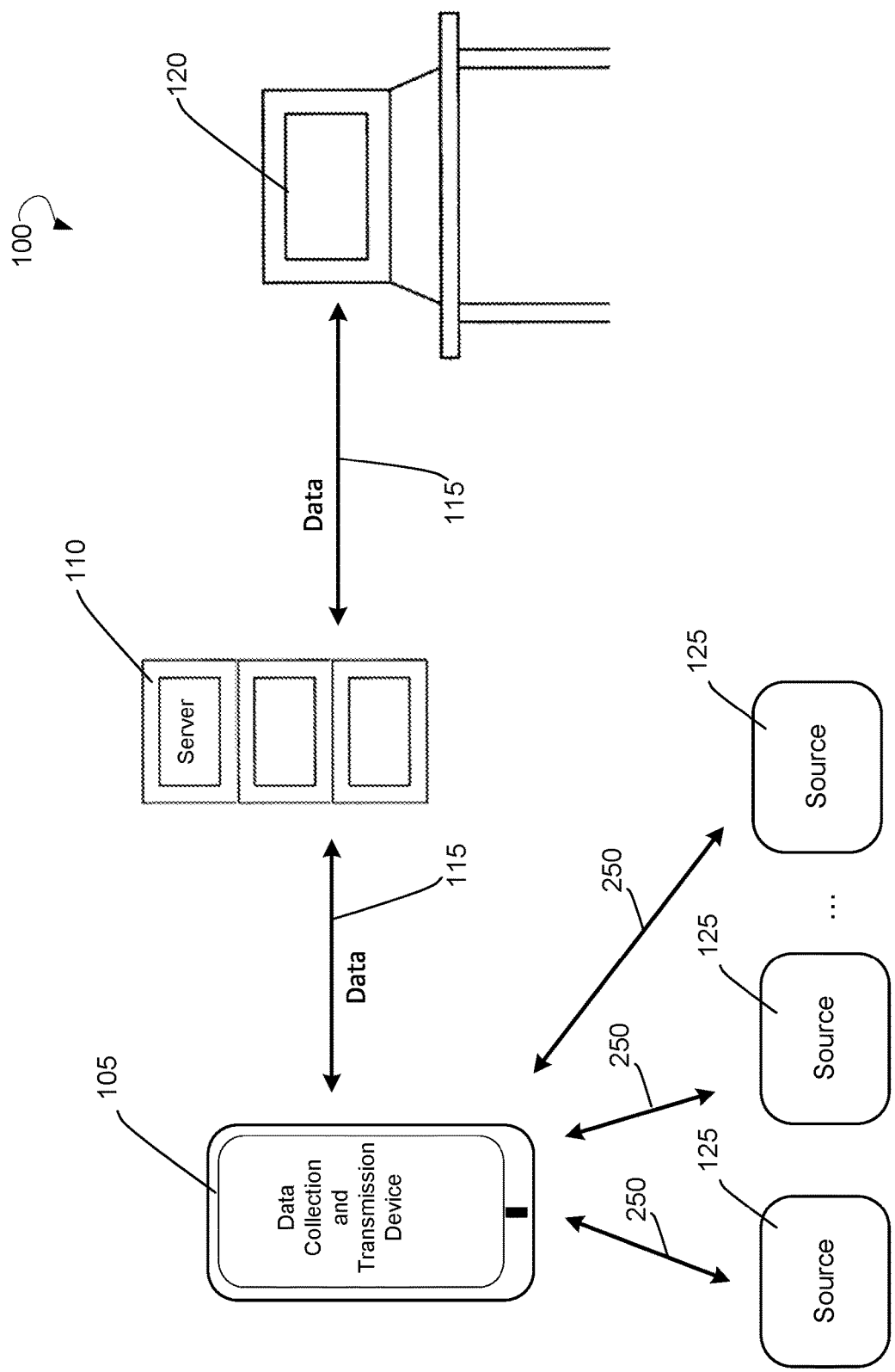
FIG. 1 illustrates an environment within which methods and systems for evaluating and transmitting combined external data from one or more sources to a central data portal can be implemented.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure is directed to systems and methods for evaluating and transmitting combined external data from one or more sources to a central data portal for processing, storage, and visualization. Some embodiments of the present disclosure may allow combining information from various and multiple data sources to be transmitted to a central data portal via a single device. The information can be obtained from persons, vehicles, machineries, assets, buildings, or outdoor locations. The information can be evaluated by methods that combine information from multiple data evaluation sources. Embodiments of the present disclosure may further aggregate data from these various sources for processing, storage, and visualization on a central data portal. Embodiments of the present disclosure may also provide one or more modes for transferring the data to the central portal.

One of the main differences between the technology disclosed herein and existing technologies is the ability to combine information from various and multiple data sources and transfer the data to a central portal. The information collected from various multiple sources can be processed and used by advanced evaluation methods to enhance system features and create new features that are not possible within the constraints of the existing technologies.

Modes of data transmission described herein are not limited to the data transmission used by existing technologies. Embodiments of the present disclosure may enhance the ability to monitor personnel both indoor and outdoor. Some embodiments of the present disclosure may allow unifying data from various sources and, thereby, provide efficacy and cost savings by eliminating the need for multiple data transmission devices.

Existing systems can be designed to take data from a single source whether it be a person, vehicle, building, or environment and then transfer the data to a portal for processing, storage, and visualization. The processing, storage and visualization data at the portal are based on the relevancy of the single source. The existing methods in which the data from a source is evaluated are also limited to the data collected from the source.

Limiting the transmission of data to a single source system requires users to access multiple single-source systems in order to review data from all sources. This separation of data limits the ability to effectively process data from multiple sources for advanced methods. Such systems are further limited by their inability to collect and evaluate data from various sources from a single device, resulting in the need to have multiple devices with redundant capabilities evaluate and transmit data.

Some embodiments of the present disclosure may provide visibility to information obtained from various sources and aggregated at a single portal. Furthermore, the transfer of data from various sources can be evaluated and transmitted using a single device. Thus, embodiments of the present disclosure may allow eliminating the need for multiple systems using multiple devices to evaluate the sources. Embodiments of the present disclosure may also provide advanced algorithms that can depend on data from multiple sources. Therefore, systems and methods disclosed herein can analyze, using aggregated source information and evaluation, the following functionalities: impact, panic, physical orientation, responsiveness, monitoring indoor and outdoor, vehicle prognostics, vehicle diagnostics, vehicle monitoring, building monitoring and access, environmental monitoring, asset monitoring, gunshot detection, and biometrics.

According to some embodiments of the present disclosure, a system for evaluating and transmitting combined external data from one or more sources to a central data portal may include a handheld microprocessor device (for example, a smart phone) and a software application running on the handheld microprocessor device. The handheld microprocessor device may collect sensor data from multiple sources for evaluation. The handheld microprocessor device may then send the data to a central data portal via wireless radio frequency (RF) communication or, optionally, by a secondary RF communication device. The secondary RF communication device can be used when the standard frequencies of the handheld microprocessor device are not sufficient to transmit the data over a distance.

The central data portal may include a computer with processing capabilities, memory, storage, and internet connection. Software programming on the central data portal can be required to receive data from the handheld microprocessor, and store, post process, and deliver data to the user interface web portal. To provide further enhancement to the evaluation and processing of data, additional devices can be used to collect data from a different source and then send the collected data to the central handheld microprocessor device.

Some embodiments of the present disclosure may allow equipping personnel with the handheld microprocessor devices that monitor sensors inherent to the devices and sensors of devices connected to the handheld microprocessor devices. The connected devices may monitor other personnel, vehicles, assets, indoor environments, and outdoor environments. Sensor data can be collected for all entities and sent through applicable transmission methods to the central data portal. All collected data can be processed and displayed via a user device on a web-portal.

Embodiments of the present disclosure may allow aggregation of data from multiple sources at a central data portal for processing and visualization. This may allow avoiding using multiple monitoring systems for a mixed fleet of different sources. The data collected by the central data portal can be used by web portal users for the following applications: general telemetry practices, safety monitoring and planning, dispatching, vehicle fleet monitoring and maintenance, emergency response and preparedness, asset monitoring, building monitoring and control, hospitality worker panic safety, indoor positioning, gunshot detection and shooter positioning, and building access.

In an example embodiment, a system for threat evaluation and data collection can include a wearable device to be worn by a user and a central data portal. The wearable device can be communicatively coupled to the central data portal and one or more external sources. The wearable device can include a sensor unit, a processor, and a communication unit. The wearable device can be configured to receive sensor data from one or more sensors installed on the wearable device and receive external sensor data from the one or more sources to evaluate statuses of the one or more external sources. The wearable device can be further configured to determine a user state based on the sensor data and statuses of the one or more external sources. The user state may be indicative of at least one physical threat to the user or at least one medical condition of the user. The wearable device can be further configured to transmit the user state and statuses of the one or more external sources to the central data portal. The central data portal may be configured to process the user state and statuses of the one or more external sources for storage and visualization.

Referring now to the drawings, FIG. 1 illustrates an environment 100 within which methods and systems for evaluating and transmitting combined external data from one or more sources to a central data portal can be implemented. The environment 100 may include a data collection and transmission device 105 (also referred to as a device 105 herein), a central data portal 115, a user interface portal 120, and one or more connected sources 125.

In some embodiments, the data collection and transmission device 105 may include a handheld microprocessor device, such as a smartphone or a tablet computer. The data collection and transmission device 105 may receive data from one or more sources 125. The sources 125 may include buildings, rooms of the buildings, outdoor locations, vehicles, and so forth. Each of the sources may include sensors, processors, actuators, and communication interface. The sources 125 can be connected to the device 105 by one or more communication channels 250 including but not limited to wireless methods of connectivity such as cellular connections, two-way radio connection, WiFi, Bluetooth™, near field communication (NFC), Satellite, Zigbee, microwave, infrared, or other protocols of wireless radio frequency (RF) connections.

The data collection and transmission device 105 may include sensors. Furthermore, the data collection and transmission device 105 may be configured to evaluate data received from the sensors and connected sources and send the data to the central data portal via communication channel 115. The data communication channel 115 may be selected from a cellular data communication channel, a two-way radio data communication channel, WiFi, Bluetooth, Near Field Communication (NFC), a satellite data communication channel, Ethernet, ZigBee, Microwave, Infrared, or other forms of wireless RF or wired data transmission. The data collection and transmission device 105 can be equipped with electronics for the transmission of data via any single mode or any combination of modes of data transfer, or any combination of cellular, two-way radio, WiFi, Bluetooth, NFC, satellite, Ethernet, ZigBee, Microwave, Infrared, or other forms of wireless RF transmission or wired data transmission.

The central data portal 110 may include one or more servers and/or cloud based computational resources. The central data portal 110 may store information received from the data collection and transmission device 105. The user interface portal 120 may include a personal computer, a tablet computer, a smartphone, and so forth. The user interface portal 120 can retrieve stored information from the central data portal 110 and send data for further processing and storage.

Figure 2:
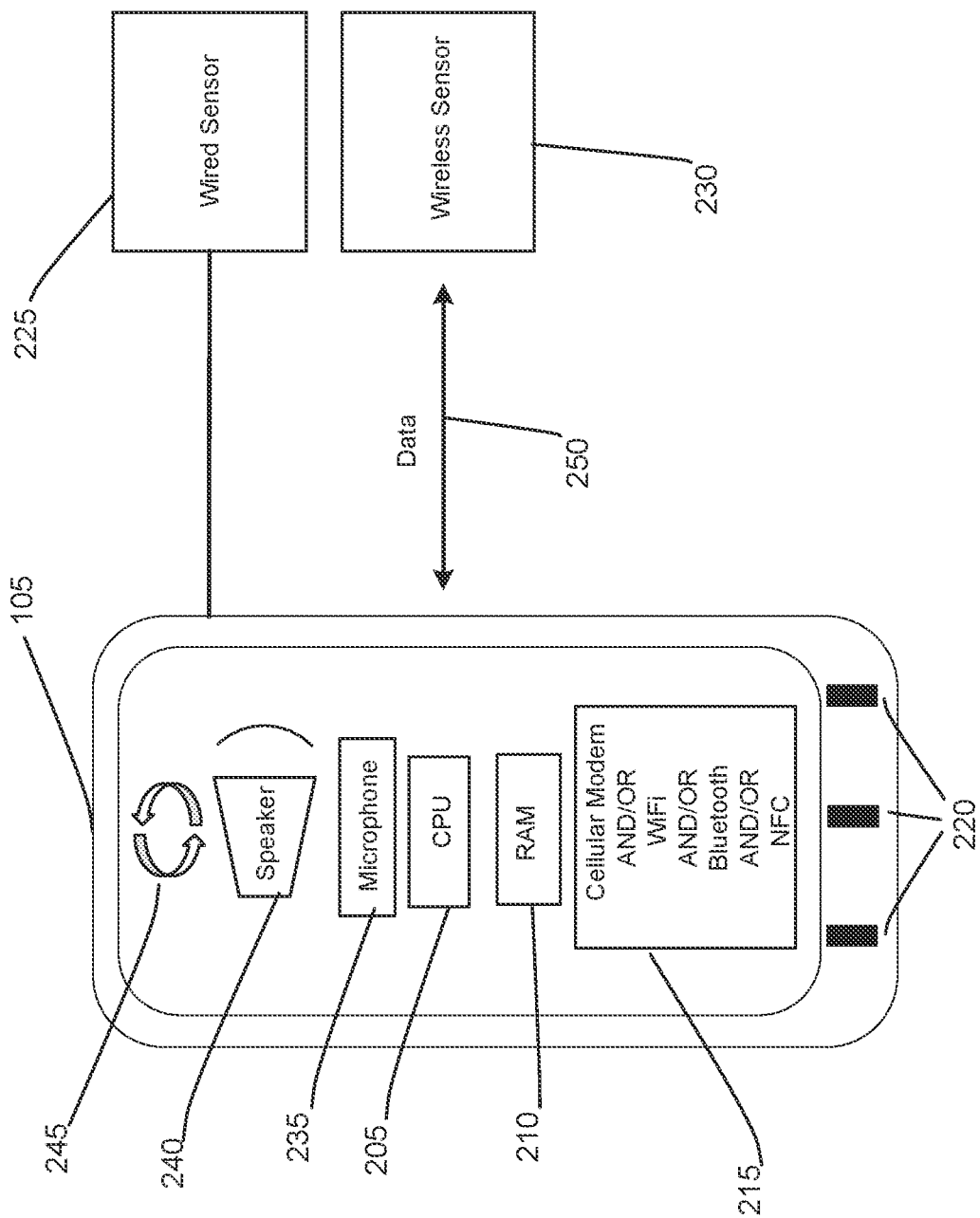
FIG. 2 is a block diagram showing an example data collection and transmission device, according to an example embodiment.

FIG. 2 is a block diagram showing an example data collection and transmission device 105, according to an example embodiment. The data collection and transmission device 105 can include a central processing unit 205 for evaluating data, memory 210 for locally storing data and a RF transmission module 215 for sending and rescinding data with the central data portal 110 (shown in FIG. 1).

The data collection and transmission device 105 can include sensors. The sensors may include sensors 220 fixed on the device 105. The sensors may include remote sensors 225 connected to the device 105 via a wired connection. The sensors may also include sensors 230 connected to the device 105 via wireless communication channels 250, such as cellular, two-way radio, WiFi, Bluetooth™, NFC, Satellite, Zigbee, Microwave, Infrared, or other forms of wireless RF connection. The sensors 220 fixed on the device 105 may include but are not limited to buttons, fingerprint sensor, temperature sensor, pressure sensor, light sensor, camera, and touch screen.

The data collection and transmission device 105 may include a microphone 235, speaker 240, and a movement sensor 245. The movement sensor may include an accelerometer and/or a gyroscope. The device 105 can be connected wirelessly to one or more of sources that include buildings, rooms, assets, person, vehicles, or outdoor locations. The device 105 can be also communicatively connected with wearable devices being worn by one or more persons.

Figure 3:
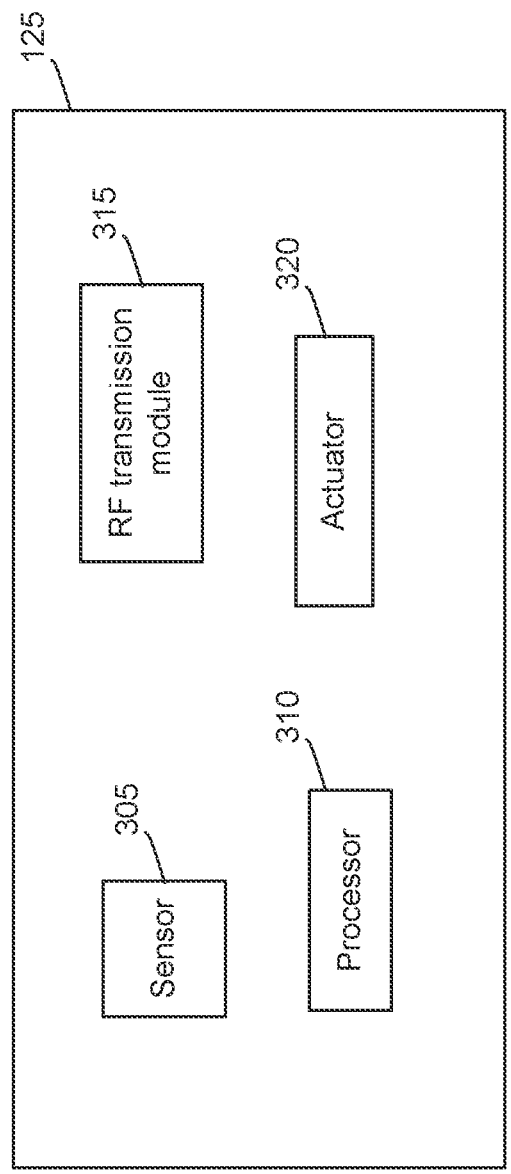
FIG. 3 is a block diagram showing a source, according to an example embodiment.

FIG. 3 is a block diagram showing a source 125, according to an example embodiment. The source 125 may include a sensor 305 and a processor 310, a RF transmission module 315, and actuator 320. The source 125 may be configured to collect data and transmit data to the device 105 and receive data from the device 105. The data between the source 125 and the device 105 can be transmitted wirelessly by communication channels 250 (shown in FIG. 1).

Figure 4:
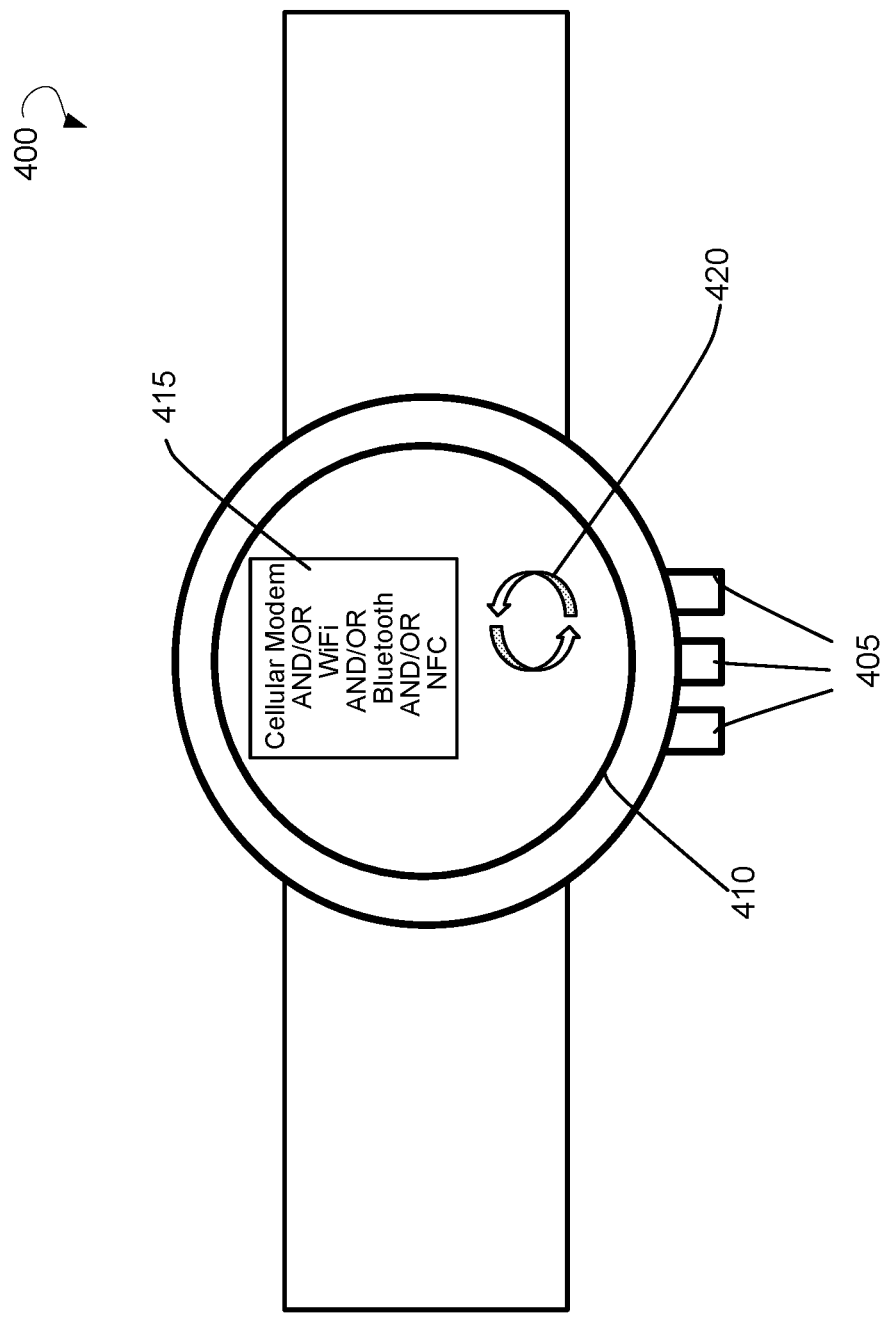
FIG. 4 is block diagram showing a wearable device, according to some example embodiment.

FIG. 4 is block diagram showing a wearable device 400, according to some example embodiments. The wearable device 400 may include sensors 405 fixed at the wearable device 400, a touch screen 410, a wireless connection module 415, and a movement sensor 420. The sensors 405 fixed at the wearable 400 can include but are not limited to buttons, fingerprint sensor, temperature sensor, pressure sensor, light sensor, camera, and heartrate sensor.

Figure 5:
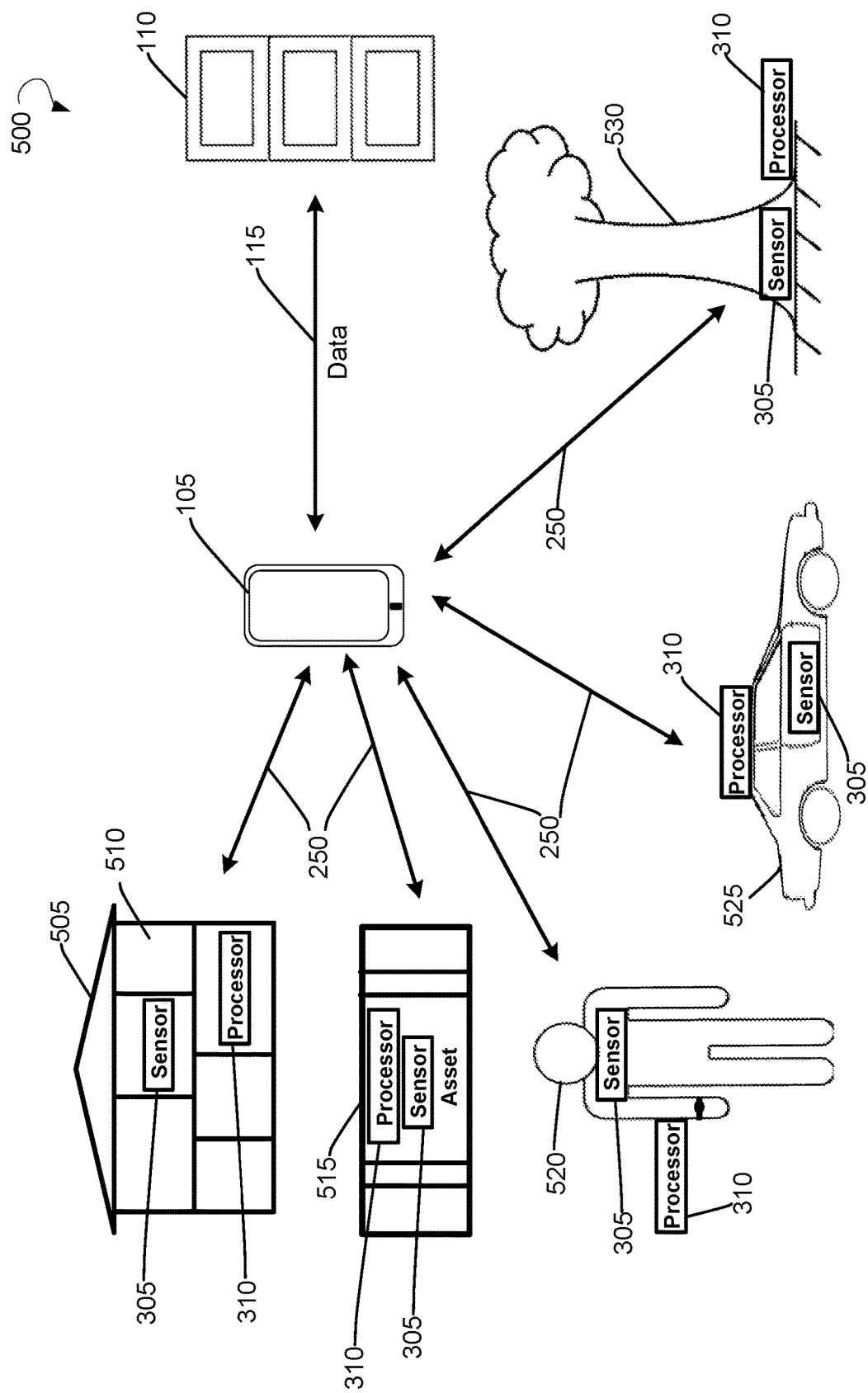
FIG. 5 illustrates an environment within which methods and systems for evaluating and transmitting combined external data from one or more sources to a central data portal can be implemented, according to some example embodiment.

FIG. 5 illustrates an environment 500 within which methods and systems for evaluating and transmitting combined external data from one or more sources to a central data portal can be implemented, according to some example embodiments. The environment 500 may include a data collection and transmission device 105, a building 505, a room 510, an asset 515, a person 520, a vehicle source 525, and outdoor location 530, a central data portal 110. Each of the sources 505, 510, 515, 520, 525, and 530 may include its own source sensor 305 and source processor 310. The sources 505, 510, 515, 520, 525, and 530 may include wireless or wired communication interface. The sources 505, 510, 515, 520, 525, and 530 may be communicatively connected with the data collection and transmission device 105 by a communication channel 250. The data collection and transmission device 105 and the central data portal 110 can be commensurately coupled via a communication channel 115.

In one embodiment of the present disclosure, the data collection and transmission device 105 may include a handheld microprocessor device with a touchscreen display, sensors, buttons, and RF transmission capabilities. The central data portal 110 may include data processing and storage hardware capable of receiving data via internet connection and publishing content to a web browser. The handheld microprocessor device may connect with other devices to collect additional information. The connection can be carried out via a wired connection (USB or similar connection) or wireless connection (Bluetooth™, NFC, Wi-Fi, cellular or similar connection) for data transmission. Each of the connected device may collect data from a source. The source can include a person, a vehicle, an asset, indoor environment (for example building and rooms), or outdoor environment. The data collected from all sources can be used to evaluate states of the sources or host source by the handheld microprocessor device (device 105).

In embodiments where the sources include one or more persons, the device 105 may collect and transmit data including, but not limited to: GPS location, time, speed, direction, orientation, impact detected, impact detected due to gunshot, gunshot detected, biometrics, heartrate, status of buttons and switches, temperature, pressure, light intensity, audio, images, files, magnetic proximity, and biometrics.

In embodiments where the sources includes one or more vehicles and assets, the handheld microprocessor device (the device 105) can collect and transmit data including, but not limited to: GPS location, time, speed, direction of vehicle, run status, fuel level, door status, crash detected, driver behavior data, gunshot detected, status of buttons and switches, temperature, pressure, light intensity, audio, magnetic proximity, Controller Area Network data, Local Interconnect Network data, Ethernet data, Serial data, Engine diagnostic data, driver status reports, odometer, driver user input display status, electronic driver logs, images, and files.

In embodiments where the sources include indoor environment or outdoor environment, the handheld microprocessor device (the device 105) can collect and transmit data from, but not limited to, the following sensors: door sensor, window sensor, gunshot detector, gas detector, and smoke detector. The data may include one or more the following:

time, GPS location, switch status, temperature, pressure, air quality, light intensity, audio, and video.

The handheld microprocessor device (the device 105) can process the received data to evaluate states of the sources. The evaluated data can be further sent to the central data portal 110 for further processing, storage, and visualization. The data from various sources can be used for advanced post processing by combining the evaluated states of the sources to calculate new states. States concerning persons may pertain, but not limited to, impact, panic, physical orientation, responsiveness, gunshot detection, health, safety conditions, state of working, active, or off duty, and location.

States concerning the vehicles and assets may pertain, but not limited to prognostics, diagnostics, running, speeding, idling, tamper, location, and safety. States concerning indoor environment and outdoor environments may pertain, but not limited to, safety, air quality, occupancy, and gunshot detected.

Figure 6:
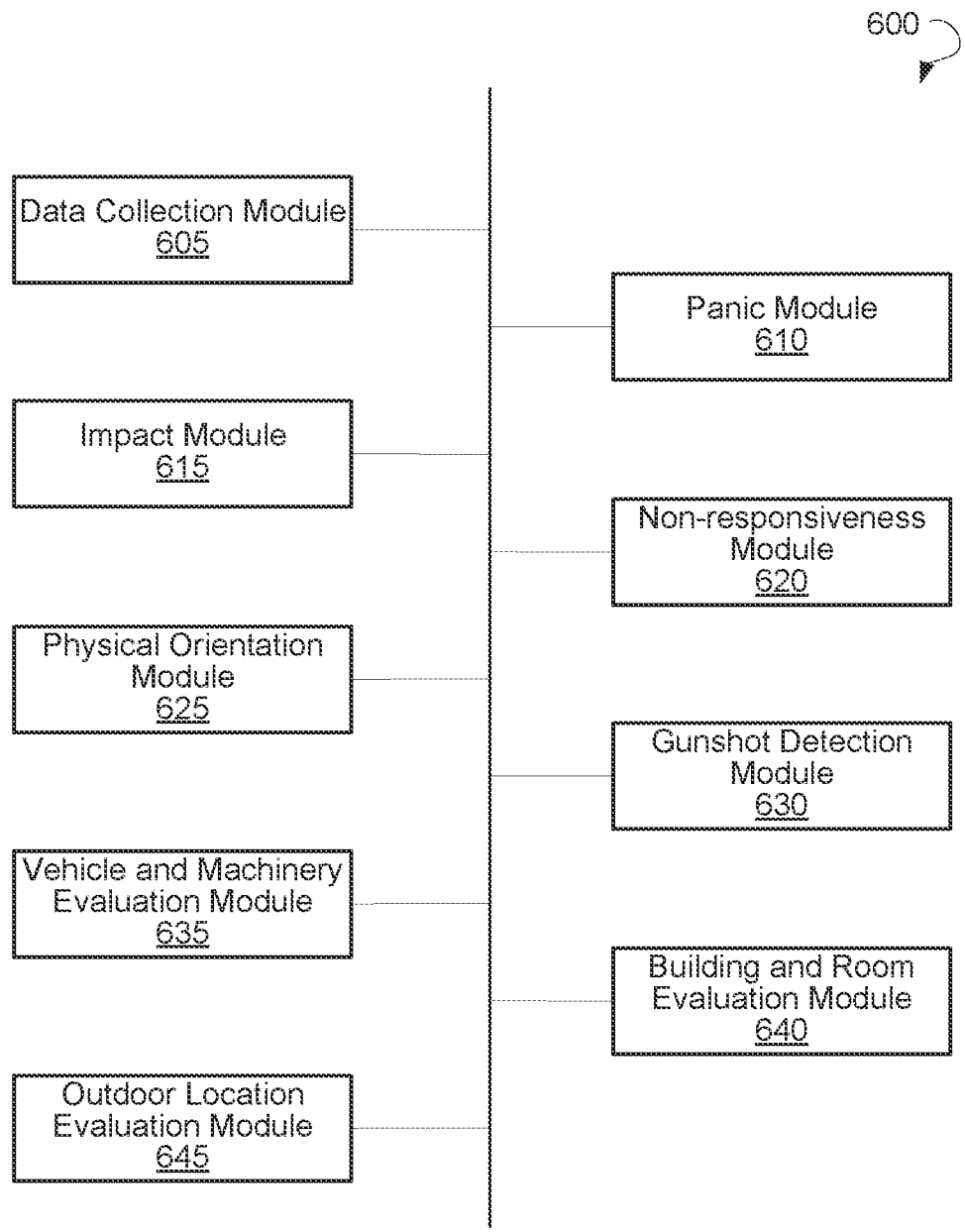
FIG. 6 is a block diagram showing various modules of a system for evaluating and transmitting combined external data from one or more sources to a central data portal, in accordance with certain embodiments.

FIG. 6 is a block diagram showing various modules of a system 600 for evaluating and transmitting combined external data from one or more sources to a central data portal in accordance with certain embodiments. Specifically, the system 600 may include a data collection module 605, a panic module 610, an impact module 615, a non-responsiveness module 620, a physical orientation module 625, a shot detection module 630, a vehicle and machinery evaluation module 635, a building and room evaluation module 640, and an outdoor location evaluation module 645. In one example embodiment, the modules of the system 600 can be implemented as processor-executable instructions stored in memory of the data collection and transmission device 105.

In some embodiments, the data collection and transmission device 105 may include a mobile device of a person. The data collection module may continuously collect data from sources, for example sources 505-530, wearable device 400 worn by a person, sensors, microphone, and movement sensor of the mobile of the data collection and transmission device 105 (mobile device of the person).

Figure 7:
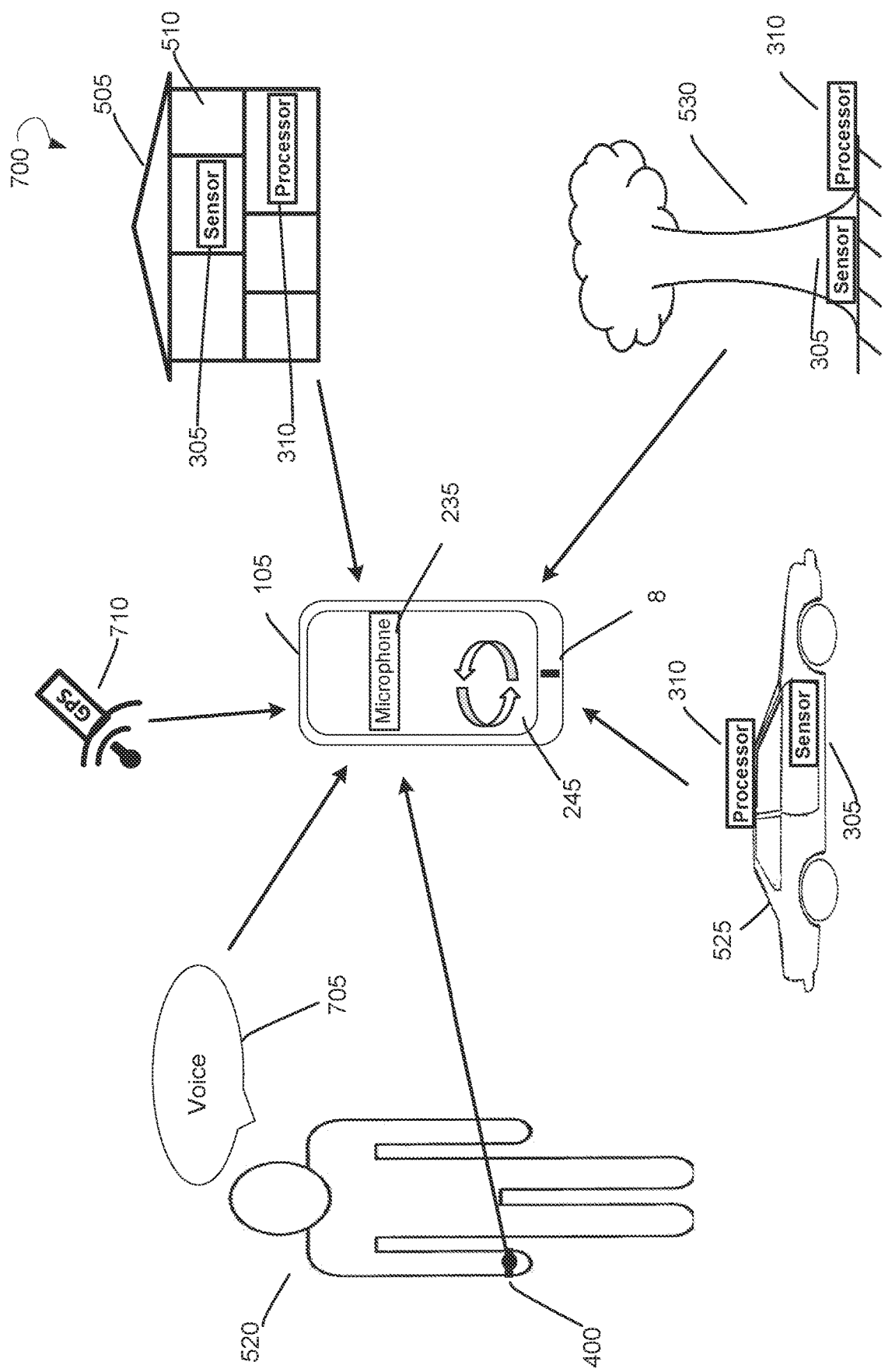
FIG. 7 illustrates an environment within which a panic module of the system for evaluating and transmitting combined external data from one or more sources to a central data portal can be implemented, according to some example embodiments.

FIG. 7 illustrates an environment 700 within which the panic module 610 of the system 600 can be implemented, according to some example embodiments. The environment 700 includes a data collection and transmission device 105, a building 505, a room 510, a person 520, a vehicle source 525, and outdoor location 530. The system 600 may be implemented as a software application on the device 105.

Panic module 610 may receive data including: voice commands and speech 705 of person 520 via microphone 235 of the data collection and transmission device 105, movement data of the device 105 via movement sensor 245, and GPS signals 710. The panic module 610 may receive data from person wearable devices 400, vehicles 525 and sensors 305 and processor 310 associated with the vehicles 525, outdoor locations 530 and sensors 305 and processor 310 associated with the outdoor locations 530, buildings 505, rooms 510 and sensors 305 and processor 310 associated with the buildings 505 and rooms 510. The panic module 610 can evaluate, based on the received data, a state of a person concerning a panic situation. Data for determining state of panic situation can be collected from inherent sensors of the device 105, connected sources, external sensors, and external stimuli.

In some example embodiments of the present disclosure, a user can trigger the panic event by pressing a button of device 105 (for example, a handheld microprocessor device). The panic event can be also triggered based on one or more of the following inputs: motion data of the device 105, voice command, result of speech analysis, touch screen button press or gesture, physical body orientation, audible gunshot detection, pressing a button on a device of connected source, and detection of a voice command by the device of connected source. The connected source can include other persons, vehicles, machineries, buildings, rooms, outdoor locations, and assets. The trigger and or sequence of triggers can be configurable and adaptable for the situation and environment. The trigger can be enabled or disabled based on the location being indoors or outdoors or a proximity to a known location, asset, building or vehicle or by manual or central data portal commanded input. Voice commands can be set by the user.

The module 610 can perform speech analysis of the voice command to determine a panic event. A video or imagery captured by the handheld microprocessor device or externally connected source device and person heartrate can be analyzed to determining a panic event. The panic event can be transmitted to the central data portal 110 for processing, storage, and visualization.

Figure 8:
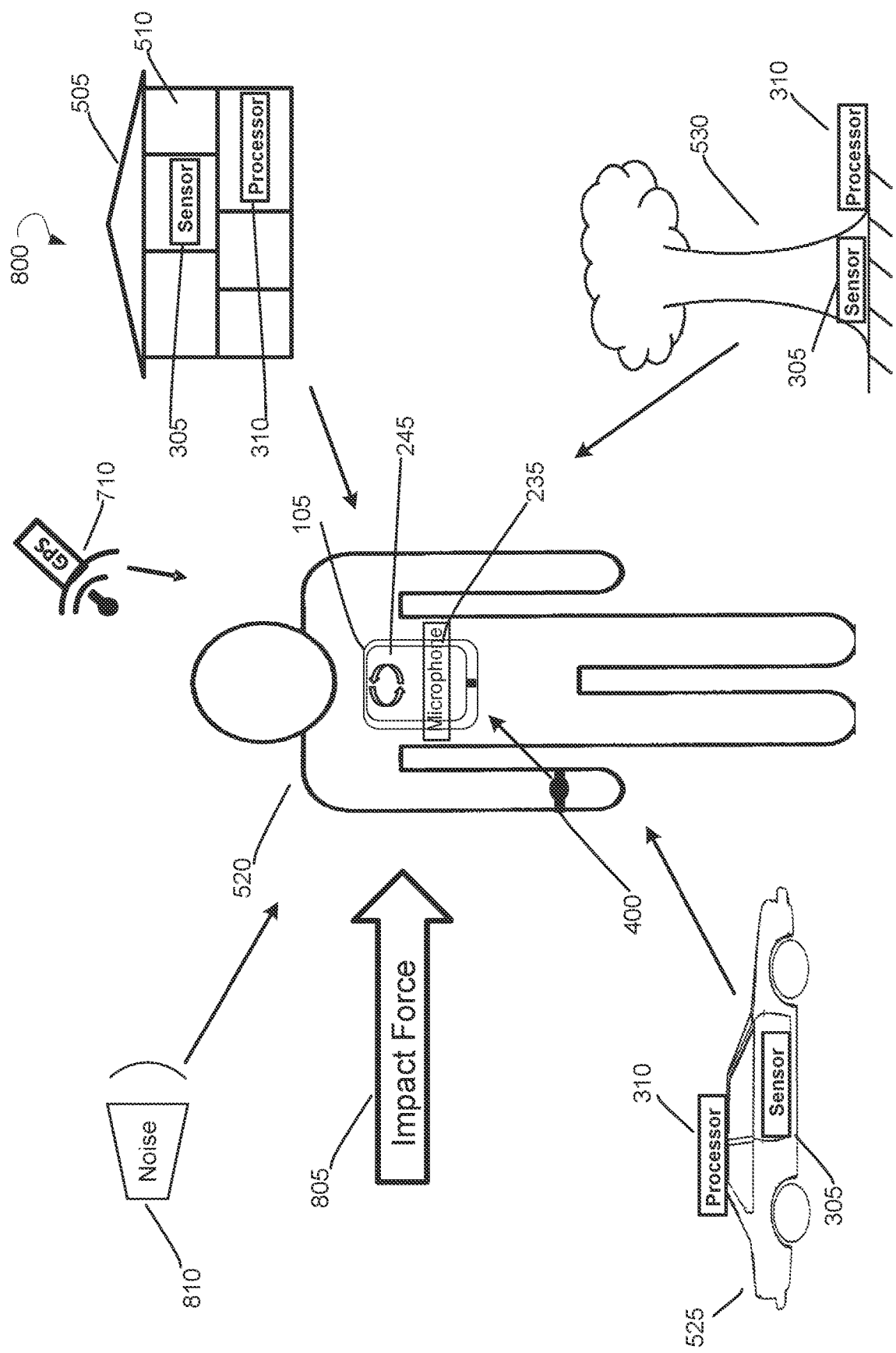
FIG. 8 illustrates an environment within which an impact module of the system for evaluating and transmitting combined external data from one or more sources to a central data portal can be implemented, according to some example embodiments.

FIG. 8 illustrates an environment 800 within which the impact module 615 of the system 600 can be implemented, according to some example embodiments. The environment 800 includes a data collection and transmission device 105, a building 505, a room 510, a person 520, a vehicle source 525, and outdoor location 530. The system 600 can run as a software application on the device 105.

The impact module 615 can receive the following data: impact force 805 via movement sensor 245 (accelerometer/gyroscope) of the device 105, environmental noise 810 via microphone 235, person 520 movement via movement sensors 245 (accelerometer/gyroscope), and GPS signals 710. The impact module 615 may receive data from person 520, wearable devices 400, vehicles 525, sensors 305, and processor 310 associated with vehicles 305, outdoor locations 530 and sensors 305 and processor 310 associated with outdoor locations 530, buildings 505, rooms 510 and sensors 305 and processor 310 associated with buildings 505 and rooms 510. The impact module 615 may evaluate, based on received data, a state of person pertaining to an impact. Data for determining the state of the person pertaining to an impact (impact event) can be collected from inherent sensors fixed on the device, connected sources, external sensors, and external stimuli.

In some embodiments of the present disclosure, the impact event can be triggered based on determination that impact force applied to a person, vehicle, or a building results in an acceleration of the device 105 (handheld microprocessor device) or a sensor connected to the device 105. The acceleration as sensed by an accelerometer and or gyroscope can be evaluated by computing amplitude of the acceleration over time in both time domain and frequency domain. The trigger and or sequence of triggers can be configurable and adaptable for the situation and environment. The trigger can be enabled or disabled based on the location indoors or outdoors or proximity to known people, location, asset, building or vehicle or by manual input or command from the central data portal 110. Other sensors and inputs can be used to evaluate the acceptance of the impact triggers. These inputs may include but are not limited to person heartrate, button press, voice command, environmental noise, audible gunshot detection, GPS signal, indoor positions, physical body orientation, connected source device button press, and connected source device voice command. The connected source may include other persons, vehicles, machineries, buildings, rooms, outdoor locations, and assets. The event data can be transmitted to the central data portal for processing, storage, and visualization.

Figure 9:
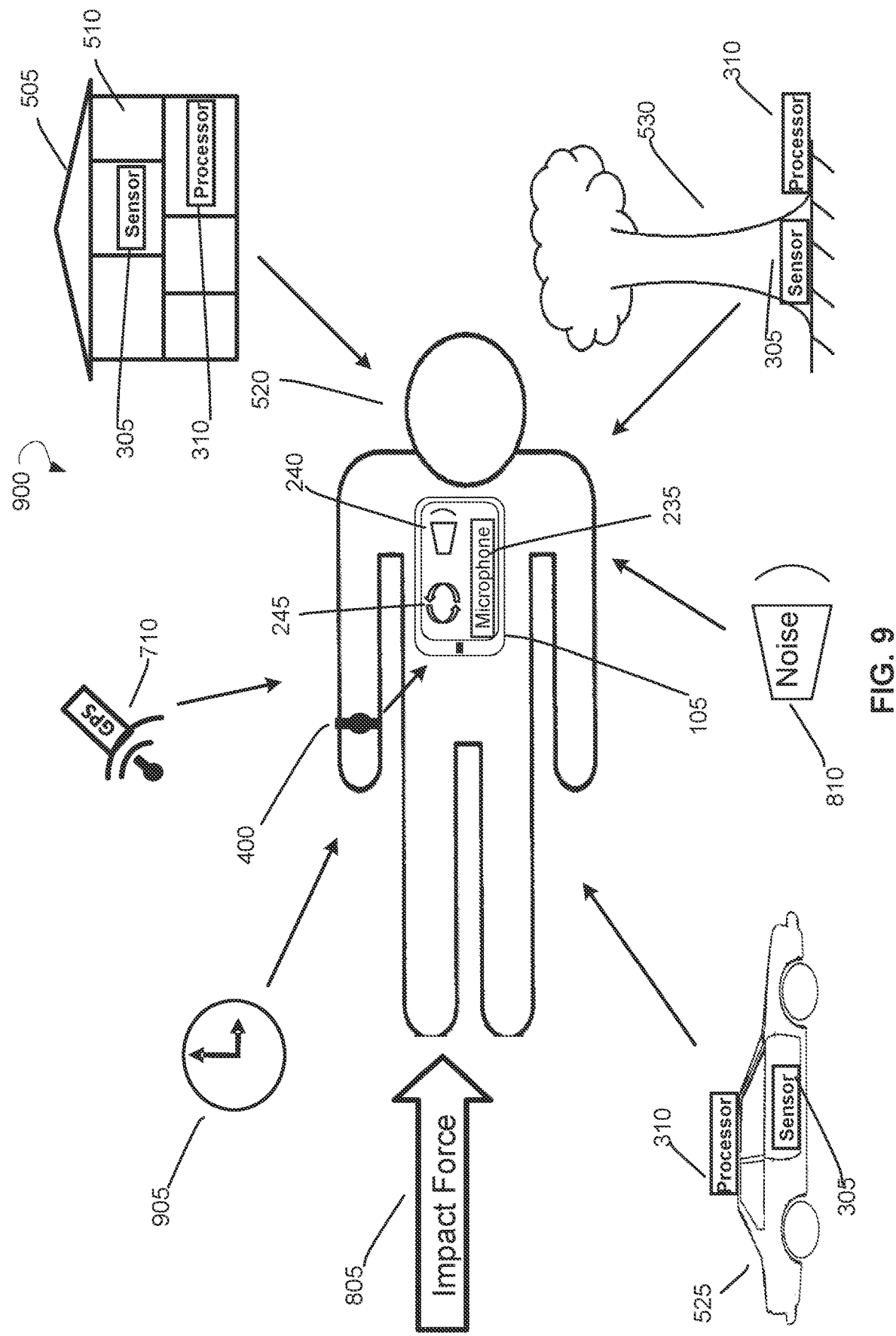
FIG. 9 illustrates an environment within which a non-responsiveness module of the system for evaluating and transmitting combined external data from one or more sources to a central data portal can be implemented, according to some example embodiments.

FIG. 9 illustrates an environment 900 within which the non-responsiveness module 620 of the system 600 can be implemented, according to some example embodiments. The environment 900 includes a data collection and transmission device 105, building 505, room 510, person 520, vehicle source 525, and outdoor location 530. The system 600 may be implemented as a software application running on the device 105.

The non-responsiveness module 620 may receive the following data: relative time 905 as calculated by the handheld microprocessor device 105, impact force 805 movement data via movement sensors 245 (accelerometer/gyroscope), environmental noise 810 detected by microphone 235, person 520 movement detected by movement sensors 245 (accelerometer/gyroscope), person 520 physical body orientation. The data can be also received from person wearable devices 400, GPS signals 710, vehicles 525 and sensors 305 and processor 310 associated with the vehicle 520, outdoor locations 530, sensors 305, processor 310 associated with outdoor locations 530, buildings 505, rooms 510, sensors 305, and processor 310 associated with the buildings 505 and rooms 510. The non-responsiveness module 620 may evaluate, based on the received data, a state of a person pertaining to the non-responsiveness. Data for determining the state of the person pertaining to the non-responsiveness can be collected from inherent sensors fixed on the device 105, connected sources, external sensors, and external stimuli.

In some embodiments of the present disclosure, a non-responsiveness event can be triggered based on a duration of time during which acceleration and or orientation of the device 105 (for example, a handheld microprocessor device) or a connected sensor is below a threshold. The threshold can be configurable and adaptable. The acceleration and or orientation as sensed by an accelerometer and or gyroscope can be evaluated by computing amplitude of the acceleration and/or orientation over time in both time domain and frequency domain. The trigger or sequence of triggers can be configurable and adaptable for the situation and environment. The trigger can be enabled or disabled based on the location of person indoors or outdoors or proximity to a known people, location, asset, building or vehicle or by manual or central data portal commanded input. Other sensors and inputs can be used to evaluate the acceptance of the non-responsiveness trigger. These inputs may include but are not limited to person's heartrate, button press, voice command, environmental noise, audible gunshot detection, GPS signal, indoor positions, physical body orientation, connected source device button press, and connected source device voice command. Connected source may include other persons, vehicles/machinery, buildings/rooms, outdoor locations, and assets. The event data can be then transmitted to the central data portal for processing, storage, and visualization.

Figure 10:
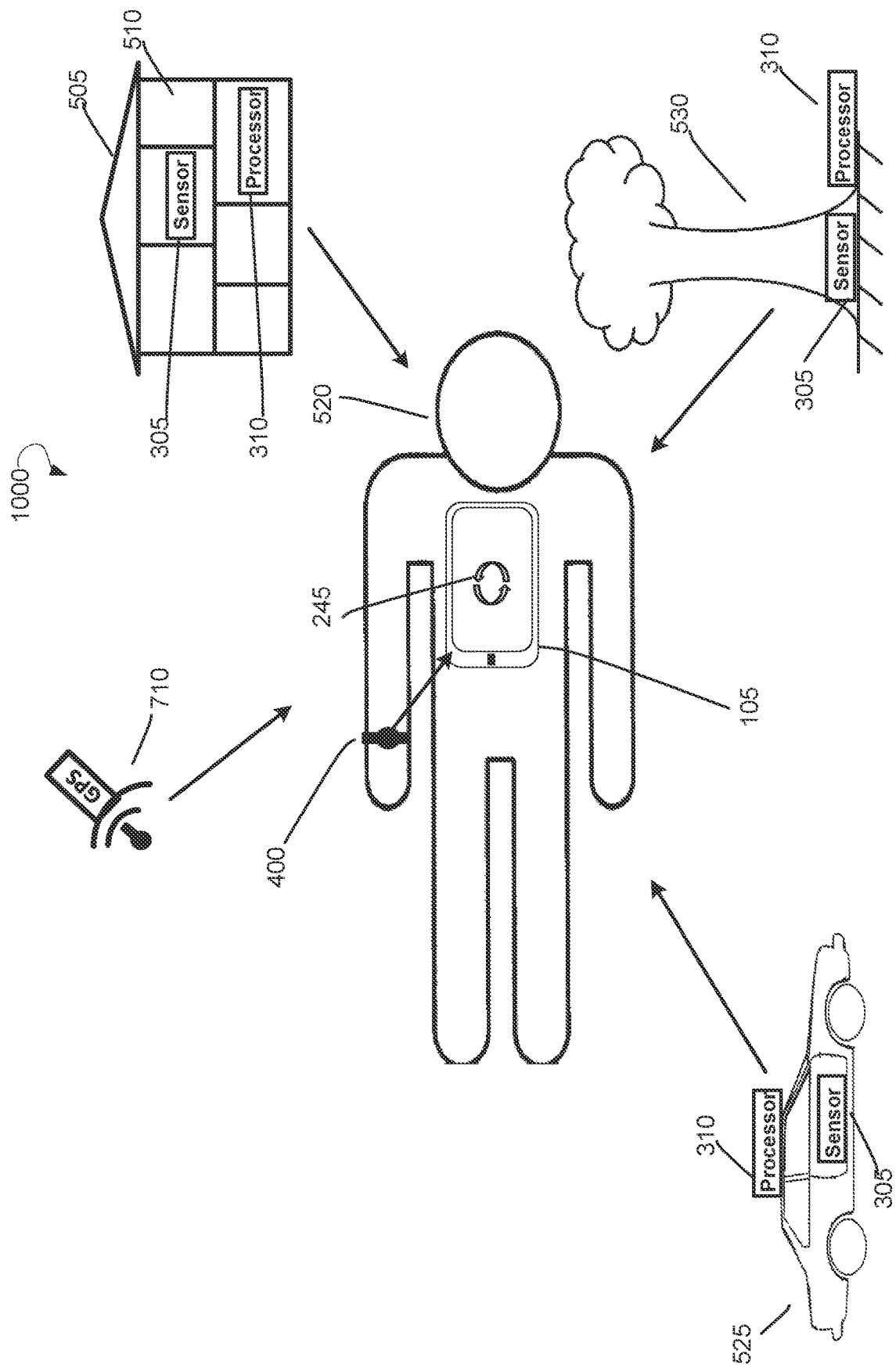
FIG. 10 illustrates an environment within which a physical orientation module of the system for evaluating and transmitting combined external data from one or more sources to a central data portal can be implemented, according to some example embodiments.

FIG. 10 illustrates an environment 1000 within which physical orientation module 625 of the system 600 can be implemented, according to some example embodiments. The environment 1000 can include a data collection and transmission device 105, building 505, room 510, person 520, vehicle source 525, and outdoor location 530. The system 600 may run as a software application on the device 105.

The physical orientation module 625 may receive data from the following sources: person 520 transferred movement via movement sensors 245 (accelerometer/gyroscope), person wearable devices 400, GPS signals 710, vehicles 525 and sensors 305 and processor 310 associated with the vehicle 520, outdoor locations 530 and sensors 305 and processor 310 associated with outdoor locations 530, buildings 505, rooms 510, sensors 305, processor 310 associated with the buildings 505, and rooms 510. The physical orientation module 625 may evaluate, based on the received data, a state of physical orientation of the person. The state pertaining to physical orientation of a person can be evaluated based on data collected from inherent sensors fixed on the device, connected sources, external sensors, and external stimuli.

In some embodiments of the present disclosure, the state of the physical orientation can be evaluated based on determination that acceleration and/or orientation to the handheld microprocessor device or connected sensor is within a threshold range. The threshold range can be configurable and adaptable. The acceleration and/or orientation as sensed by an accelerometer and or gyroscope can be evaluated by computing an amplitude of the acceleration or orientation over time in both time domain and frequency domain. The state and/or sequence of states can be configurable and adaptable for the situation and environment. The determination of the state can be enabled or disabled based on the location of person indoors or outdoors or proximity to known people, location, asset, building or vehicle or by manual or central data portal commanded input. Other sensors and inputs can be used to evaluate the acceptance of the orientation state. These inputs may include but are not limited to button press, GPS signal, indoor positions, connected wearable device orientation, connected source device button press. Connected source may include other persons, vehicles/machinery, buildings/rooms, outdoor locations, and assets. The state of the physical orientation to the person can be transmitted to the central data portal for processing, storage, and visualization.

Figure 11:
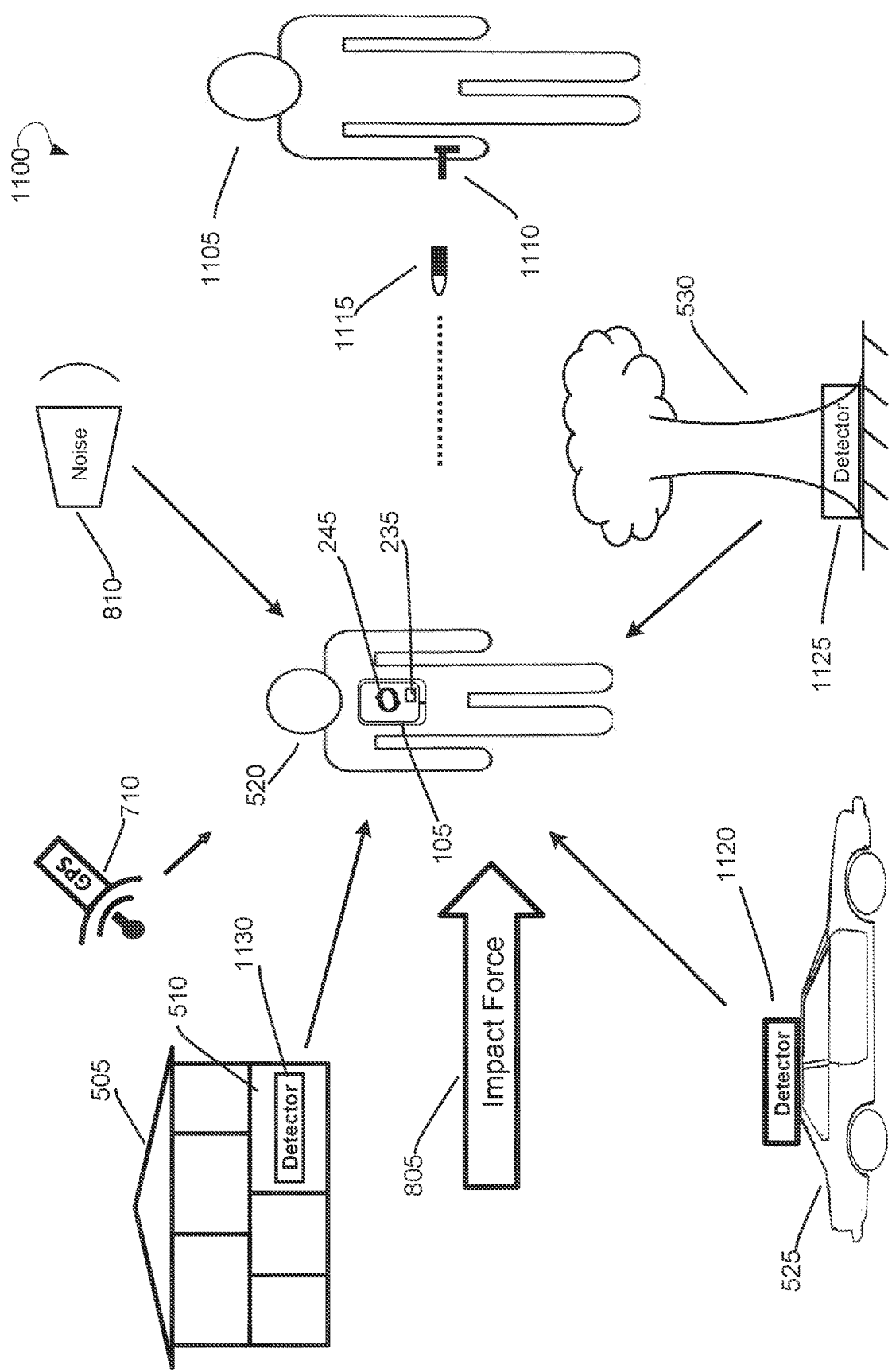
FIG. 11 illustrates an environment within which a gunshot detection module of the system for evaluating and transmitting combined external data from one or more sources to a central data portal can be implemented, according to some example embodiments.

FIG. 11 illustrates an environment 1100 within which gunshot detection module 630 of the system 600 can be implemented, according to some example embodiments. The environment 1100 includes a data collection and transmission device 105, building 505, room 510, person 520, vehicle source 525, outdoor location 530, shooter 1105, firearm 1110, and bullet 1115. The system 600 may be implemented to run as a software application on the device 105.

The gunshot detection module 630 can be configured to detect the presence of an audible gunshot of a bullet 1115 from firearm 1110 and the location of the shooter 1100. The shot detection module 630 may receive the following data: impact force 805 movement via movement sensors 245 (accelerometer/gyroscope), environmental noise (810) via microphone 235, and GPS signals 710. The data can be also received from person wearable devices 400, vehicles 520 and vehicle detectors 1120, outdoor locations 530 and associated outdoor detectors 1125, buildings 505 and rooms 510 and their associated indoor detectors 1130. The gunshot detection module 630 may evaluate, based on the received data, a state of gunshot detected status. Data for detection of gunshot can be collected from inherent sensors of the device 105, connected sources, external sensors, and external stimuli.

In some embodiments of the present disclosure, the device 105 may trigger a gunshot detection event by determining that audible input is above a threshold. The threshold can be configurable and adaptable. The audible input due to a firearm discharging and projectile can be detected by microphone of the handheld microprocessor device or connected sensor. The audible input as sensed by the microphone can be evaluated by computing the amplitude of the audible input over time in both time domain and frequency domain. The trigger and or sequence of triggers can be configurable and adaptable for the situation and environment. The trigger can be enabled or disabled based on the location of person indoors or outdoors or proximity to a known people, asset, building or vehicle or by manual input or command from central data portal. Other sensors and inputs can be used to evaluate the acceptance of the shot detection trigger. These inputs may include but are not limited to person's heartrate, button press, voice command, environmental noise, GPS signal, indoor positions, connected source device button press, and connected source device audio input. The connected source can include other persons, vehicles, machineries, buildings, rooms, outdoor locations, and assets. The event data can be transmitted to the central data portal for processing, storage, and visualization.

Figure 12:
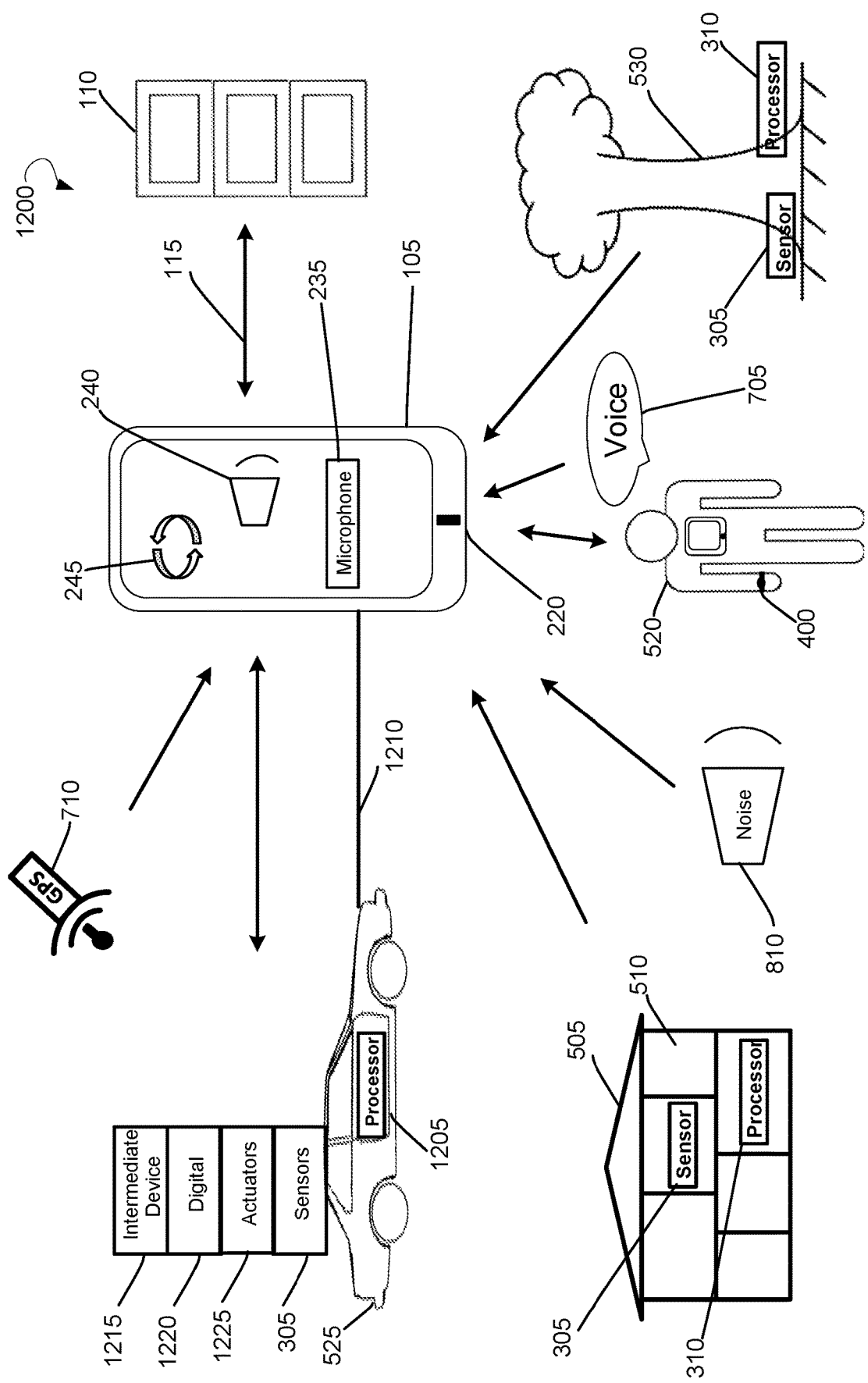
FIG. 12 illustrates an environment within which a vehicle and machinery evaluation module of the system for evaluating and transmitting combined external data from one or more sources to a central data portal can be implemented, according to some example embodiments.

FIG. 12 illustrates an environment 1200 within which vehicle and machinery evaluation module 630 of the system 600 can be implemented, according to some example embodiments. The environment 1200 includes a data collection and transmission device 105, building 505, room 510, person 520, vehicle 525, and outdoor location 530, and central data portal 110. The system 600 may run as a software application on the device 105.

The vehicle and machinery evaluation module 630 may receive data from a vehicle 525. Data may be pertaining to the vehicle's past, current and future performance and operation running state as evaluated by vehicle processor 1205. The data can be transmitted to the data collection and transmission device 105 via a wired connection 1210 or wirelessly. The device 105 may receive the vehicle's data directly from the vehicle 525 or via an intermediate vehicle communication and processing device 1215. Sensor data from sensors 305 and digitally communicated vehicle and machinery data 1220 can be transmitted to the device 105 and then to the central data portal 110 over communication channel 115.

The device 105 can receive commands from a person 520 and or central data portal 110 to actuate actuators 1225 and/or modify data of the vehicle processor 1205 on the vehicle 525. The device 105 can receive commands from a person 520 and or central data portal 110 to modify data or command outputs of the vehicle intermediate vehicle communication and processing device 1215. Upon receiving the command outputs, the intermediate vehicle communication and processing device 1215 can actuate one or more states of the vehicle 525. The states may include, but are not limited to, one or more of the following: a vehicle running state, states of lights, states of pumps, states of doors, and states of windows.

Connected sensors and sources can be used for the mutual evaluation of the sensors associated with vehicle 525 and person 520 and other sources. The sources may include the following: GPS signals 710, other vehicles and sensors and processor associated with other vehicles, outdoor locations 530 and sensors 305 and processor 310 associated with the outdoor locations, buildings 505 and rooms 510, sensors 305 and processor 310 associated with buildings 505 and rooms 510, and person wearable devices 400. The evaluation can be based on the following data: person 520 movement detected via movement sensors 245 (accelerometer/gyroscope), voice commands and speech 705 detected via microphone 240, environmental noise 810 detected via microphone 240, data from bio-metrics sensors either inherent to the device 105 or external to the device 105, verbal passwords, and visual passwords. Motions or RF communications can be used to allow/deny access to vehicle 525 for person 520 by way of unlocking/locking or opening/closing passageways.

In some embodiments, the data for evaluation of state of vehicle 525 and person 520 can be collected from inherent sensors fixed on the device 105 (the handheld microprocessor device), vehicle connected to the device 105, external sensors, and external stimuli. The device 105 may collect data from the vehicle via a wired or wireless connection. Data can be collected directly from the vehicle or through an intermediate communication and processing device. The digitally communicated vehicle data collected either directly or through the intermediate device can be in the form of an industry standard protocol. The industry protocols may include but are not limited to SAE J1939, SAE J1708, SAE J1587, OBD-II, CAN FD, CAN 2.0 A/B, LIN, Flexray, RS-232, Modbus, CANopen.

The data collected from the vehicle can be evaluated to determine vehicle's performance, diagnostics, and prognostics. The data for evaluation can be received from other sensors and sources. The data may include but are not limited to: person's heartrate, button press, voice command, environmental noise, bio-metrics for vehicle access to door lock state and powertrain run state, audible gunshot detection, GPS signal, indoor positions, gas detection, smoke detection, temperature, video and images, impact force imposed on the handheld microprocessor device, physical body orientation, connected source device button press, and connected source device voice command. Connected source may include other persons, vehicles, machineries, buildings, rooms, outdoor locations, and assets.

The interface between the vehicle 525 and the device 105 (for example, a handheld microprocessor device) may include a graphical display of the handheld microprocessor device or connected intermediate device. The graphical display may provide feedback concerning vehicle performance, diagnostics, and prognostics. The graphical display may provide a mode for additional user input. Evaluations can be configurable and adaptable for the situation and environment. The evaluation can be enabled or disabled based on the location of the vehicle and whether the person is indoors or outdoors or the proximity to a known person, location, asset, building, or vehicle. The evaluation can be enabled by manual input or command from the central data portal. The evaluated data can be transmitted to the central data portal for processing, storage, and visualization.

Figure 13:
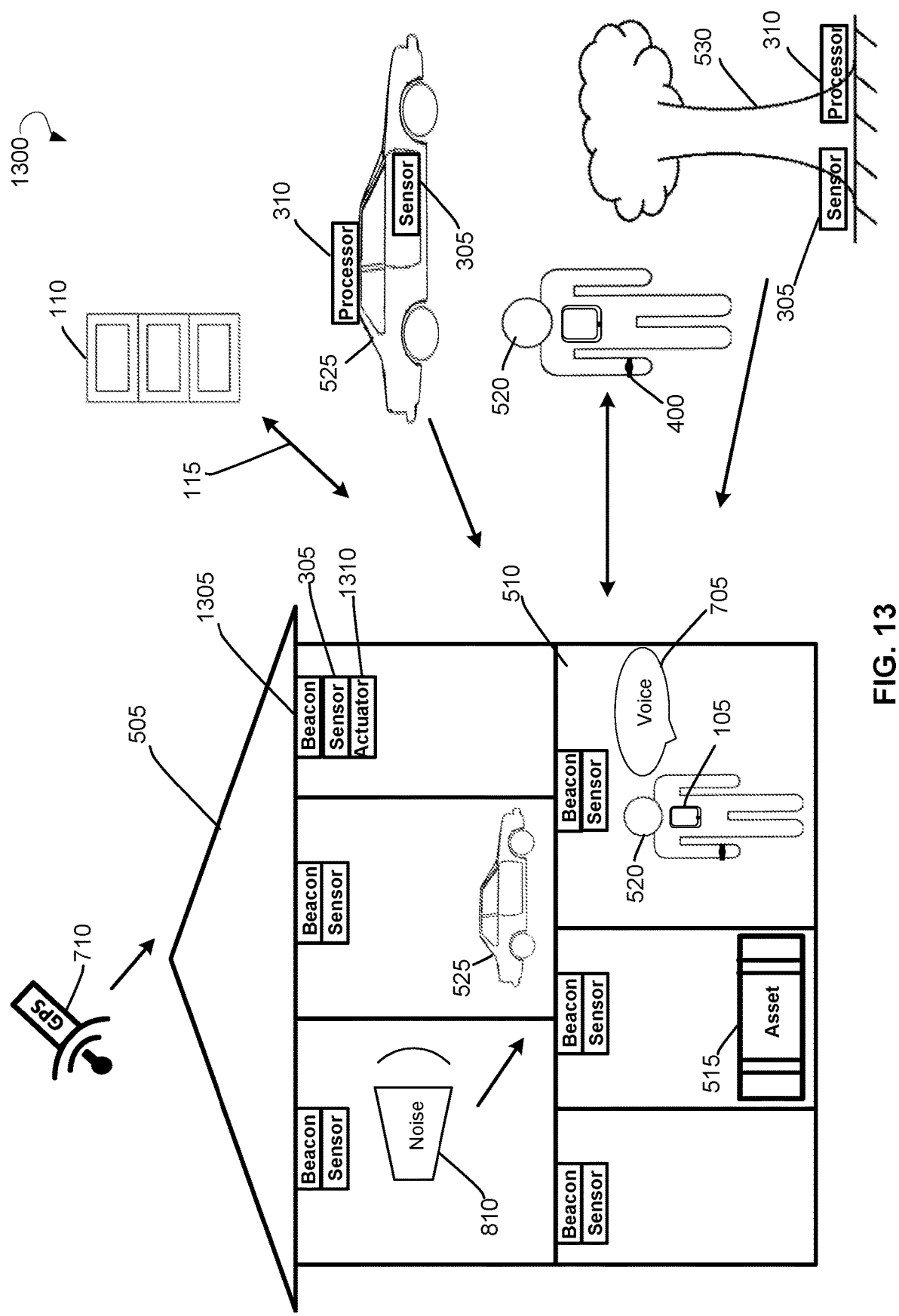
FIG. 13 illustrates an environment within which a building and room evaluation module of the system for evaluating and transmitting combined external data from one or more sources to a central data portal can be implemented, according to some example embodiments.

FIG. 13 illustrates an environment 1300 within which building and room evaluation module 635 of the system 600 can be implemented, according to some example embodiments. The environment 1300 includes a data collection and transmission device 105, building 505, room 510, person 520, vehicle 525, outdoor location 530, and central data portal 110. The system 600 may run as a software application on the device 105.

The building and room evaluation module 635 may receive data from a connected room sensor 305 or beacon 1305. Data can pertain to states of the building and room and environment of the building and room. The data can be transmitted to the device 105 via wireless data connectivity. Data can be transmitted to the device 105 and then to the central data portal 110 via a communication channel 115.

Connected sensors and sources can be used for the mutual evaluation of the buildings 505, rooms 510, and host person 520. The sensors may include but are not limited to door open detectors, window open detectors, temperature sensors, smoke detector, gas detector, fire detector, humidity sensors, air quality sensors, gunshot detector, lock, door barricade deployment, explosion detectors, glass break detectors, door impact detectors, wall impact detectors, and GPS signals 710. The data can be obtained from other buildings and rooms and sensors and beacons associated with the other buildings and rooms, outdoor locations 530 and associated sensors 305 and processor 310, and person's wearable devices 400. The data may include voice commands and speech detected via microphone 235 (shown in FIG. 2), or environmental noise detected via microphone 235.

The device 105 can receive commands from a person 520 or central data portal 110. The commands can be generated as a result of evaluation of the building and/or room. The commands can result in actuation of room actuators 1310. Beacons 1305, other sensors, and sensors of the device 105 can be used for determining positions of people 520, assets 515 and vehicles 525 within the building 505 or room 510. Bio-metrics sensors either inherent to the device 105 or external to the device 105, verbal passwords, visual passwords, motion, or RF communication can be used to allow/deny access to building 505 and/or room 510 for person 520 by way of unlocking/locking or opening/closing passageways.

The building and room evaluation module 635 may evaluate state of the building, room, and person both individually and collectively. Data for the evaluation can be collected from inherent sensors fixed on the device 105 (for example, a handheld microprocessor device), sensors/beacons/processor of connected room, external sensors, and external stimuli.

In some embodiments, the handheld microprocessor device may collect data from the building/room via a wireless connection. Data can be collected directly from the building/room or through an intermediate communication and processing device. The data collected from the building/room can be evaluated to determine building/room status. The evaluation may also be based on data from other sensors and sources. These data may include but are not limited to: person heartrate sensor, button press, voice command, environmental noise, bio-metrics for building/room access to passageway lock state, audible gunshot detection, GPS signal, indoor positions, gas detection, smoke detection, temperature, humidity, air quality, video and images, impact force imposed on handheld microprocessor device, physical body orientation, connected source device button press, connected source device voice command. Connected source may include other persons, vehicles/machinery, buildings/rooms, outdoor locations, and assets.

In some embodiments, interface between the building/room and handheld microprocessor device may include a graphical display of the handheld microprocessor device or connected intermediate device. The graphical display may provide feedback on building/room status. The graphical display may provide a mode for additional user input. Evaluations of status of building or room can be configurable and adaptable for the situation and environment. The evaluation can be enabled or disabled based on the location indoors or outdoors or proximity to a known person, location, asset, building or vehicle or by manual or central data portal commanded input. The evaluated data can be transmitted to the central data portal for processing, storage, and visualization.

Figure 14:
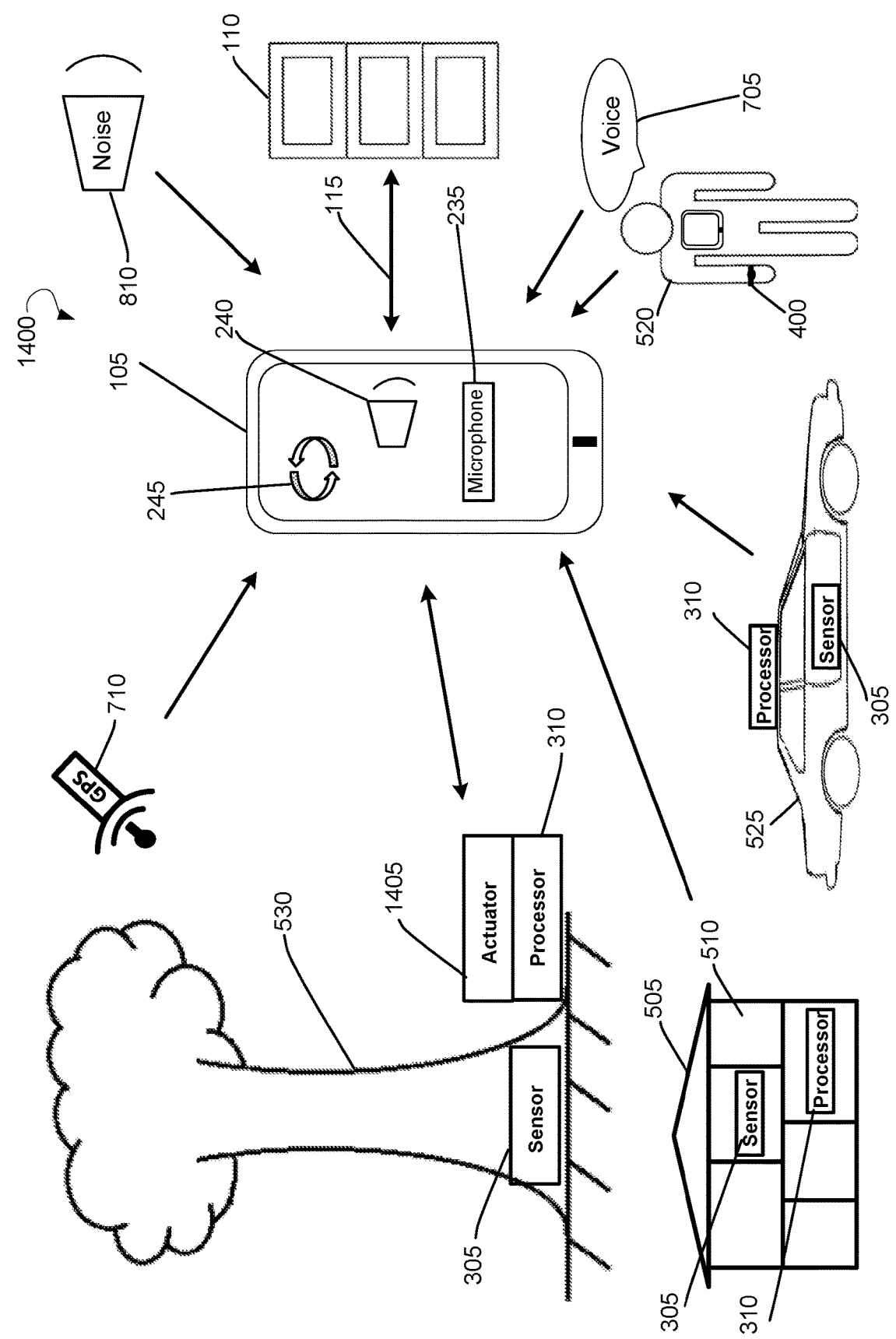
FIG. 14 illustrates an environment within which an outdoor location evaluation module of the system for evaluating and transmitting combined external data from one or more sources to a central data portal can be implemented, according to some example embodiments.

FIG. 14 illustrates an environment 1400 within which outdoor location evaluation module 635 of the system 600 can be implemented, according to some example embodiments. The environment 1300 includes a data collection and transmission device 105, a building 505, a room 510, person 520, a vehicle 525, and outdoor location 530, and central data portal 110. The system 600 may run as a software application on the device 105.

The outdoor location evaluation module will receive data from a connected outdoor location 530 and sensors 305 and processor 310 associated with the outdoor location. The data may pertain to the outdoor location environment. The data can be transmitted to the device 105 via wireless communication channel. Data can be further transmitted from the device 105 to the central data portal 110 via communication channel 115.

Connected sensors and sources can be used for the mutual evaluation of the outdoor location 530 and host person 520. The sensors may include but are not limited to a temperature detector, smoke detector, gas detector, fire detector, humidity detector, air quality detector, gunshot detector, and explosion detector. The sources may include GPS signals 710, other outdoor locations and sensors and processors associated with the other outdoor locations, buildings 505, rooms 510, and sensors 305 and processors 505 associated with the buildings 505 and rooms 510, person 520 movement and transferred movement to movement sensors 345 (accelerometer/gyroscope), person wearable devices 420, voice commands and speech 705 via microphone 235, and environmental noise 810 via microphone 235. The device 105 can receive commands from a person 520, central data portal 110. The command can be generated based result of evaluation of the outdoor location. The commands can result in actuation of outdoor actuators 1405.

The outdoor location evaluation module 635 and may be configured to evaluate states the outdoor location and person both individually and collectively. Data can be collected from inherent sensors fixed on the handheld microprocessor device, connected outdoor location sensors and processors, and external sensors and external stimuli.

In some embodiment of the present disclosure, the device 105 (for example, a handheld microprocessor device) may collect data from the outdoor location 530 via a wireless connection. Data can be collected directly from the outdoor location or through an intermediate communication and processing device. The data collected from the location 530 can be used for evaluation of outdoor location status. The evaluation of the outdoor location status can be also based on data received from other sensors and sources. The data may include but are not limited to person's heartrate, button press, voice command, environmental noise, data of audible gunshot detectors, GPS signal, indoor positions, data of gas detectors, data of smoke detectors, temperature, humidity, air quality, video and images, impact force imposed on handheld microprocessor device, physical body orientation, connected source device button press, and connected source device voice command. The connected source may include other persons, vehicles/machinery, buildings/rooms, other outdoor locations, and assets.

The outdoor location evaluation module 635 may provide and an interface between the outdoor location and handheld microprocessor device via a graphical display of the handheld microprocessor device or connected intermediate device. The graphical display may provide feedback on outdoor location status. The graphical display may provide a mode for additional user input. Evaluations of status of outdoor location can be configurable and adaptable based on situation and environment. The evaluation can be enabled or disabled based on the location indoors or outdoors or proximity to a known person, location, asset, building or vehicle. The evaluation can be enabled by manual input or command from central data portal. The evaluated data can be transmitted to the central data portal for processing, storage, and visualization.

Figure 15:
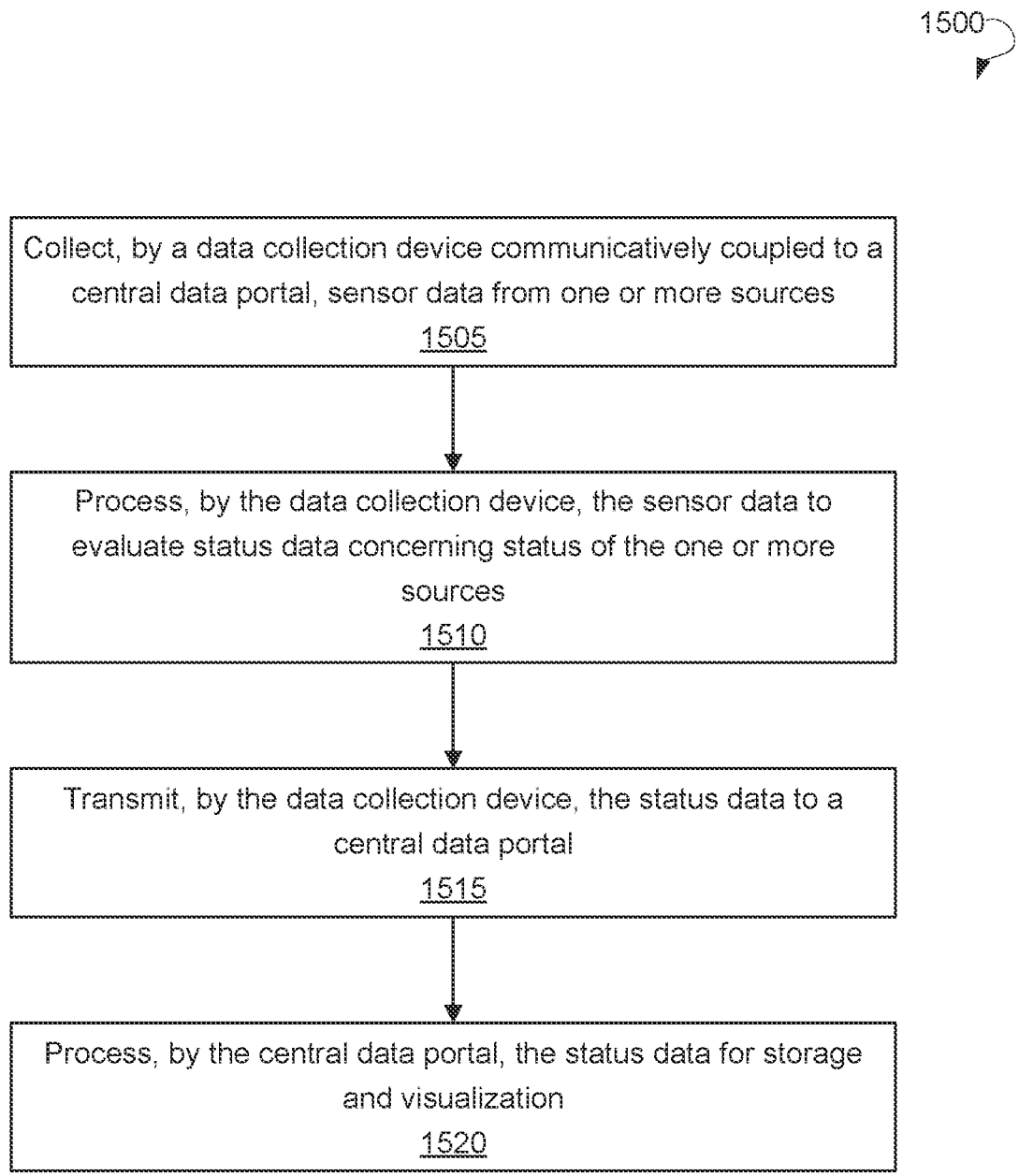
FIG. 15 is a flow chart showing a method for evaluating and transmitting combined external data from one or more sources to a central data portal, according to some example embodiments.

FIG. 15 is flow chart illustrating a method 1500 for evaluating and transmitting combined external data from one or more sources to a central data portal. The method 1500 can be performed within environment 100 shown in FIG. 1 or environment 700 shown in FIG. 7.

The method 1500 may commence, in block 1505, with collecting, by a data collection device communicatively coupled to a central data portal, sensor data from one or more sources. In block 1510, the method 1500 may proceed with processing, by the data collection device, the sensor data to evaluate status data concerning status of the one or more sources. In block 1515, the method 1500 may proceed with transmitting, by the data collection device, the status data to a central data portal. In block 1520 may proceed with processing, by the central data portal, the status data for storage and visualization.

Figure 16:
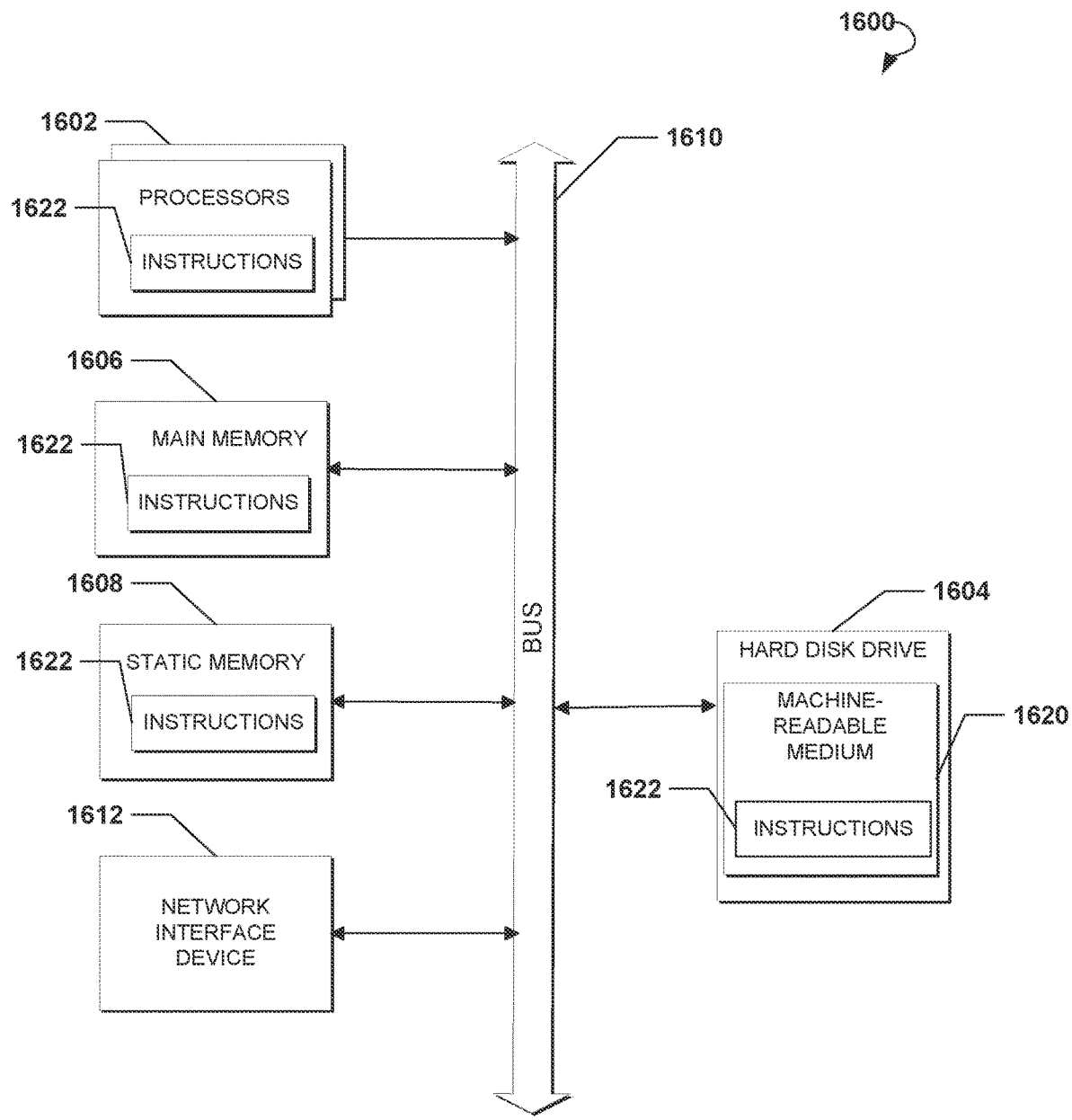
FIG. 16 shows a computing system that can be used to implement a method for evaluating and transmitting combined external data from one or more sources to a central data portal, according to an example embodiment.

FIG. 16 shows a diagrammatic representation of a computing device for a machine in the exemplary electronic form of a computer system 1600, within which a set of instructions for causing the machine to perform any one or more of the methodologies discussed herein can be executed. In various exemplary embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a PC, a tablet PC, a set-top box, a cellular telephone, a digital camera, a portable music player (e.g., a portable hard drive audio device, such as an Moving Picture Experts Group Audio Layer 3 (MP3) player), a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1600 may include a processor or multiple processors 1602, a hard disk drive 1604, a main memory 1606, and a static memory 1608, which communicate with each other via a bus 1610. The computer system 1600 may also include a network interface device 1612. The hard disk drive 1604 may include a computer-readable medium 1620, which stores one or more sets of instructions 1622 embodying or utilized by any one or more of the methodologies or functions described herein. The instructions 1622 can also reside, completely or at least partially, within the main memory 1606 and/or within the processors 1602 during execution thereof by the computer system 1600. The main memory 1606 and the processors 1602 also constitute machine-readable media.

While the computer-readable medium 1620 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, NAND or NOR flash memory, digital video disks, Random Access Memory, Read-Only Memory, and the like.

The example embodiments described herein may be implemented in an operating environment comprising software installed on a computer, in hardware, or in a combination of software and hardware.

In some embodiments, the computer system 1600 may be implemented as a cloud-based computing environment, such as a virtual machine operating within a computing cloud. In other embodiments, the computer system 1600 may itself include a cloud-based computing environment, where the functionalities of the computer system 1600 are executed in a distributed fashion. Thus, the computer system 1600, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud may be formed, for example, by a network of web servers that comprise a plurality of computing devices, such as the computer system 1600, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

Figure 17:
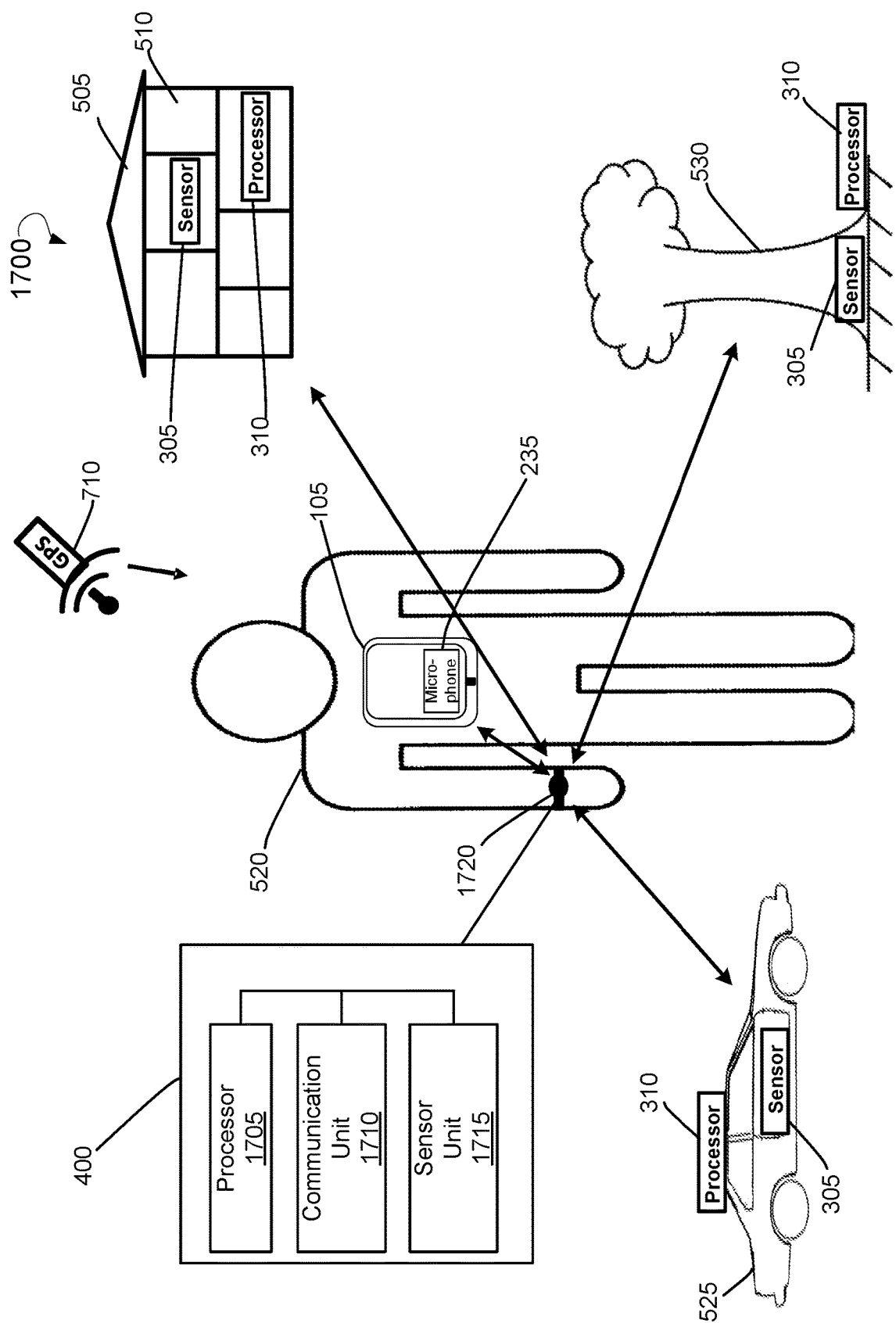
FIG. 17 shows a system for threat evaluation and data collection, according to some example embodiments.

FIG. 17 shows a system 1700 for threat evaluation and data collection, according to some example embodiments. The system 1700 may include a wearable device 400 configured to be worn by a user shown as a person 520 and a central data portal (such as the central data portal 110 as shown in FIG. 5). The wearable device 400 may include a processor 1705, a communication unit 1710, and a sensor unit 1715. The communication unit 1710 of the wearable device 400 may be communicatively coupled to the central data portal and one or more external sources. The one or more external sources may include a building 505, a room 510, a car shown as a vehicle source 525, and an outdoor location 530. In some embodiments, the one or more external sources may further include personal computing devices of the user, such as the data collection and transmission device 105. In an example embodiment, the wearable device 400 may further include a housing 1720 to hold the processor 1705, the communication unit 1710, and the sensor unit 1715. The housing 1720 may be implemented in one of the following shapes: glasses, a watch, a ring, and so forth. The system 1700 can run as a software application on the device 105.

The sensor unit 1715 of the wearable device 400 may be configured to receive sensor data from one or more sensors installed on the wearable device 400. The wearable device 400 may be configured to receive, via the processor 1705, the sensor data from the sensor unit 1715 and receive, via the communication unit 1710, external sensor data from the one or more external sources. In an example embodiment, the one or more sensors may be configured to measure at least one physiological parameter of the user. The at least one physiological parameter may include one of the following: a heart rate, blood pressure, electrocardiogram, blood oxygen saturation level, and the like. In a further example embodiment, the one or more sensors may be configured to measure one or more of the following: a position and motion of the user.

The wearable device 400 can be further configured to process, via the processor 1705, the sensor data and the external sensor data to evaluate a user state. The user state may be indicative of at least one physical threat to the user or at least one medical condition of the user. In an example embodiment, the evaluation of the user state may include detecting a sudden change in the at least one physiological parameter of the user. In a further example embodiment, the evaluation of the user state may include detecting a sudden change of the position or the motion of the user.

Therefore, in various example embodiments, the wearable device 400 may be used to detect a physical threat to the user and/or a medical condition of the user. For example, the wearable device 400 may detect a sudden change in physiological parameters of the user, such as a heart rate, blood pressure, body perspiration, and the like. The wearable device 400 may process the physiological parameters by using predetermined algorithms and determine that the sudden change in the physiological parameters is caused by a physical threat to the user, such as a gunshot.

When the user is diagnosed with a disease or medical condition or takes medications prescribed by a healthcare specialist, the data related to the disease, medical condition, and medications can be processed and used to tune the predetermined algorithms. In an example embodiment, baseline parameters can be determined for the user based on a chronic disease or medical condition of the user. The wearable device 400 can detect a change in physiological parameters of the user, for example, a blood oxygen saturation level dropping 10% below a threshold level or an electrocardiogram of the user deviating from a reference electrocardiogram or a previous electrocardiogram of the user. The wearable device 400 can process the physiological parameters based on the predetermined algorithms and, optionally, baseline parameters, and determine that the user has a medical condition. In an example embodiment, the wearable device 400 may analyze the collected data to determine whether the medical condition is associated with a chronic disease or is indicative of a medical emergency condition.

The wearable device 400 can be further configured to transmit, via the communication unit 1710, the user state to the central data portal. The central data portal can be configured to process the user state for storage and visualization.

In an example embodiment, the wearable device 400 can act as a gateway to a plurality of devices in order to facilitate communications with the central data portal. The plurality of devices can include stationary hospital devices, medical devices, other wearable devices worn by the user, wearable devices worn by other users, devices located in a proximity of the user, and so forth. In an example embodiment, the stationary hospital device can be connected to the user and/or be located in the proximity of the user in order to collect data associated with the user, such as physiological parameters of the user. The communication unit 1710 of the wearable device 400 can be communicatively connected to the stationary hospital device and collect, via the communication unit 1710, data from the stationary hospital device. The wearable device 400 can transmit the data collected from the stationary hospital device to the central data portal. The central data portal may process the data collected by the stationary hospital device. In an example embodiment, the wearable device 400 and/or the central data portal may correlate the data collected by the wearable device 400 and the data collected by external sources, such as the stationary hospital device, and determine the user state based on the correlated data.

In an example embodiment, physiological parameters of the user can be continuously monitored by the wearable device 400 and one or more stationary hospital devices or medical devices in case of a disease and/or medical condition or suspected cases of various types of diseases, including those diseases caused by the coronavirus family of viruses such as a severe acute respiratory syndrome (SARS), Middle East respiratory syndrome (MERS), and coronavirus disease 2019 (COVID-19). The wearable device 400 may collect the sensor data from one or more sensors installed on the wearable device 400 and the external sensor data from the one or more stationary hospital devices or medical devices. The wearable device 400 can process the sensor data and/or the external sensor data to evaluate a user state and transmit the user state to the central data portal. In some embodiments, the wearable device 400 transmits the sensor data collected by the wearable device 400 and/or the external sensor data collected by the one or more external sources to the central data portal.

In an example embodiment, the processor 1705 of the wearable device 400 can be configured to determine or actuate statuses of the one or more external sources. The processor 1705 can be configured to determine the user state based on a correlation between the statuses of the one or more external sources. The statuses may include one of the following: a humidity level at the outdoor location outside of a pre-determined humidity range, air temperature at the outdoor location outside of a pre-determined temperature range, air quality level at the outdoor location outside of a pre-determined air quality range, gunshot detected at the outdoor location, smoke detector alarm at the outdoor location, gas detector alarm at the outdoor location, unlocked room, locked room, open window, closed window, temperature of the room higher than a pre-determined temperature threshold, smoke detector alarm, gas detector alarm in the building, fire detector alarm in the building, humidity level in the room outside a pre-determined humidity range, air quality level in the room outside a pre-determined air quality range, gunshot in the building or the room detected, window glass broken, door impacted, wall impacted, and so forth.

Figure 18:
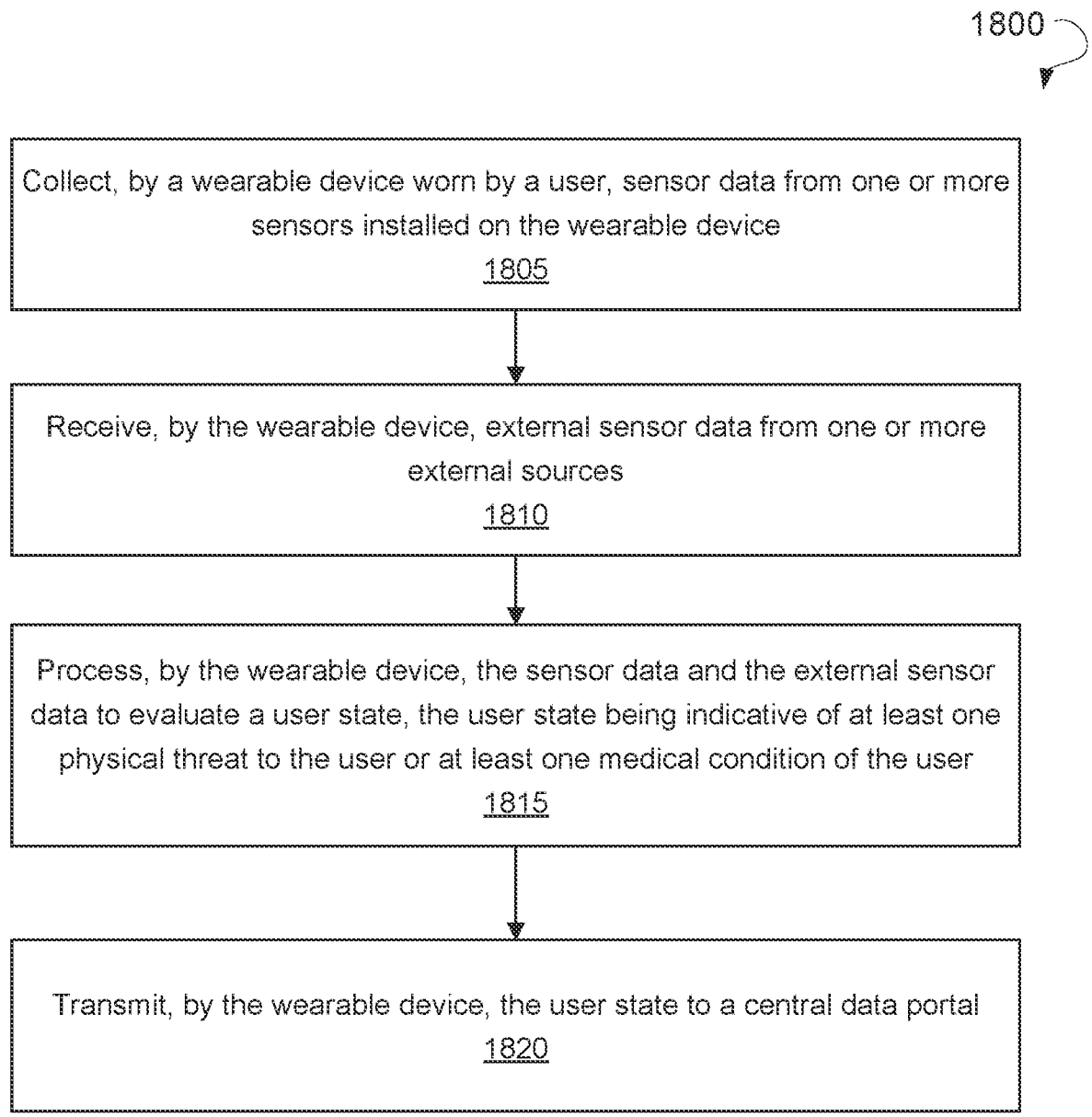
FIG. 18 is a flow chart showing a method for threat evaluation and data collection, according to some example embodiments.

FIG. 18 is a flow chart showing a method 1800 for threat evaluation and data collection, according to some example embodiments. The method 1800 may commence with collecting, by a wearable device, sensor data from one or more sensors installed on the wearable device at step 1805. The wearable device may be worn by a user. The wearable device may include a processor, sensor unit, and communication unit communicatively coupled to a central data portal and one or more external sources. The sensor unit may be configured to measure at least one physiological parameter of the user. In further example embodiments, the sensor unit may be configured to measure a position and/or a motion of the user. The wearable device may be carried out in one of the following shapes: glasses, watch, ring, and so forth.

The method 1800 may include receiving external sensor data from the one or more external sources at step 1810. In an example embodiment, the method 1800 may further include collecting, by the wearable device, data from a stationary hospital device.

The method 1800 may continue with processing, at step 1815, the sensor data and the external sensor data to evaluate a user state. The user state can be indicative of at least one physical threat to the user or at least one medical condition of the user. The evaluation of the user state may include detecting a sudden change in the at least one physiological parameter. The at least one physiological parameter can include one or more of the following: a heart rate, blood pressure, electrocardiogram, blood oxygen saturation level, and the like. In further example embodiments, the evaluation of the user state may include detecting a sudden change of the position and the motion of the user.

In an example embodiment, the method 1800 may include determining or actuating, by the wearable device, statuses of the one or more external sources. The one or more external sources can include one of the following: a building, room, outdoor location, car, personal computing devices of the user, and so forth. The user state can be evaluated based on the correlation between the statuses of the one or more external sources.

The method 1800 may further include transmitting the user state to the central data portal at step 1820. In an example embodiment, the method 1800 may include transmitting, by the wearable device, the data from the stationary hospital device to the central data portal. The central data portal may be configured to process the user state and/or the data from the stationary hospital device for storage and visualization.

Thus, wearable devices, systems, and methods for threat evaluation and data collection are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A wearable device for threat evaluation and data collection, the wearable device to be worn by a user and comprising:
   a processor;
   a memory associated with the processor;
   a sensor unit configured to receive sensor data from one or more sensors installed on the wearable device; and
   a communication unit communicatively coupled to a central data portal and one or more external sources, wherein the processor is configured to:
   receive the sensor data from the sensor unit;
   receive, via the communication unit, external sensor data from the one or more external sources;
   receive, from the memory, baseline physiological parameters associated with the user, the baseline physiological parameters including predetermined physiological parameters for the user based on preprocessed data associated with a health condition of the user;
   process the sensor data and the external sensor data based on the baseline physiological parameters to evaluate a user state, the user state being indicative of at least one physical threat to the user due to a physical impact applied to an external object and at least one medical condition of the user, the at least one physical threat to the user due to the external object being determined based on statuses of the one or more external sources, the statuses being determined based on the external sensor data received from the one or more external sources, wherein the evaluation of the user state includes determination that a change in the at least one medical condition of the user is caused by the at least one physical threat; and
   transmit the user state to the central data portal, wherein the central data portal is configured to process the user state for storage and visualization,
   wherein the one or more sensors are configured to measure one or more of following: a position and a motion of the user; and the evaluation of the user state includes detecting a sudden change of the position or the motion of the user.

2. The wearable device of claim 1, further comprising a housing to hold the processor, the sensor unit, and the communication unit, the housing being carried out in one of following shapes: glasses, a watch, and a ring.

3. The wearable device of the claim 1, wherein the one or more sensors are configured to measure at least one physiological parameter of the user; and wherein the evaluation of the user state includes detecting a sudden change in the at least one physiological parameter.

4. The wearable device of the claim 3, wherein the at least one physiological parameter includes one of following: a heart rate, a blood pressure, an electrocardiogram, and a blood oxygen saturation level.

5. The wearable device of the claim 1, wherein: the communication unit is communicatively connected to a stationary hospital device; and the processor is configured to: collect, via the communication unit, data from the stationary hospital device; and
   transmit the data from the stationary hospital device to the central data portal.

6. The wearable device of the claim 1, wherein the processor is configured to determine or actuate the statuses of the one or more external sources.

7. The wearable device of the claim 6, wherein the one or more external sources include one of following: a building, a room, an outdoor location, a car, and a personal computing device of the user.

8. The wearable device of the claim 7, wherein the statuses include one of following: a humidity level at the outdoor location outside of a pre-determined humidity range, an air temperature at the outdoor location outside of a pre-determined temperature range, an air quality level at the outdoor location outside of a pre-determined air quality range, a gunshot detected at the outdoor location, a smoke detector alarm at the outdoor location, a gas detector alarm at the outdoor location, an unlocked room, a locked room, an open window, a closed window, a temperature of the room higher than a pre-determined temperature threshold, a smoke detector alarm in the building, a gas detector alarm in the building, a fire detector alarm in the building, a humidity level in the room outside the pre-determined humidity range, an air quality level in the room outside the pre-determined air quality range, a gunshot in the building or the room detected, a window glass broken, a door impacted, and a wall impacted.

9. The wearable device of the claim 6, wherein the processor is configured to determine the user state based on a correlation between the statuses of the one or more external sources.

10. A method for threat evaluation and data collection, the method comprising:
- collecting, by a wearable device to be worn by a user and comprising a processor, a memory associated with the processor, a sensor unit, and a communication unit, communicatively coupled to a central data portal and one or more external sources, sensor data from one or more sensors installed on the wearable device;
- receiving, by the wearable device, external sensor data from the one or more external sources;
- receiving, by the wearable device from the memory, baseline physiological parameters associated with the user, the baseline physiological parameters including predetermined physiological parameters for the user based on preprocessed data associated with a health condition of the user;
- processing, by the wearable device, the sensor data and the external sensor data based on the baseline physiological parameters to evaluate a user state, the user state being indicative of at least one physical threat to the user due to a physical impact applied to an external object and at least one medical condition of the user, the at least one physical threat to the user due to the external object being determined based on statuses of the one or more external sources, the statuses being determined based on the external sensor data received from the one or more external sources, wherein the evaluation of the user state includes determination that a change in the at least one medical condition of the user is caused by the at least one physical threat; and
- transmitting, by the wearable device, the user state to the central data portal, wherein the central data portal is configured to process the user state for storage and visualization,
- wherein the sensor unit is configured to measure one or more of following: a position and a motion of the user; and the evaluation of the user state includes detecting a sudden change of the position and the motion of the user.

11. The method of the claim 10, wherein the wearable device is carried out in one of the following shapes: glasses, a watch, and a ring.

12. The method of the claim 10, wherein the sensor unit is configured to measure at least one physiological parameter of the user; and wherein the evaluation of the user state includes detecting a sudden change in the at least one physiological parameter.

13. The method of the claim 12, wherein the at least one physiological parameter includes one or more of following: a heart rate, a blood pressure, an electrocardiogram, and a blood oxygen saturation level.

14. The method of the claim 10, further comprising: collecting, by the wearable device, data from a stationary hospital device; and transmitting, by the wearable device, the data from the stationary hospital device to the central data portal.

15. The method of the claim 10, further comprising determining or actuating, by the wearable device, the statuses of the one or more external sources.

16. The method of the claim 15, wherein the one or more external sources include one of the following: a building, a room, an outdoor location, a car, and personal computing devices of the user.

17. The method of the claim 15, wherein the user state is evaluated based on correlation between the statuses of the one or more external sources.

18. A system for threat evaluation and data collection, the system comprising:
- a central data portal; and
- a wearable device to be worn by a user, the wearable device communicatively coupled to the central data portal and one or more external sources, the wearable device including a sensor unit, a processor, a memory associated with the processor, and a communication unit, the wearable device being configured to:
- receive sensor data from one or more sensors installed on the wearable device;
- receive external sensor data from the one or more external sources to evaluate statuses of the one or more external sources; receive, from the memory, baseline physiological parameters associated with the user, the baseline physiological parameters including predetermined physiological parameters for the user based on preprocessed data associated with a health condition of the user;
- evaluate, based on the sensor data, the baseline physiological parameters, and the statuses of the one or more external sources a user state, the user state being indicative of at least one physical threat to the user due to a physical impact applied to an external object and at least one medical condition of the user, the at least one physical threat to the user due to the external object being determined based on the statuses of the one or more external sources, the statuses being determined based on the external sensor data received from the one or more external sources, wherein the evaluation of the user state includes determination that a change in the at least one medical condition of the user is caused by the at least one physical threat; and
- transmit the user state and the statuses of the one or more external sources to the central data portal, wherein the central data portal is configured to process the user state and the statuses of the one or more external sources for storage and visualization,
- wherein the sensor unit is configured to measure one or more of following: a position and a motion of the user; and the evaluation of the user state includes detecting a sudden change of the position and the motion of the user.

* * * * *